United States Patent
Becher et al.

(10) Patent No.: US 10,159,247 B2
(45) Date of Patent: *Dec. 25, 2018

(54) HERBICIDE FORMULATIONS CONTAINING AN ETHERAMINE AND ALKYLAMINE ALKOXYLATE SURFACTANT SYSTEM

(71) Applicant: Monsanto Technology LLC, St. Louis, MO (US)

(72) Inventors: David Z. Becher, St. Louis, MO (US); David Eaton, Kirkwood, MO (US); John Hemminghaus, Crestwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,464

(22) Filed: Nov. 23, 2015

(65) Prior Publication Data

US 2016/0192647 A1 Jul. 7, 2016

Related U.S. Application Data

(63) Continuation of application No. 12/635,166, filed on Dec. 10, 2009, now Pat. No. 9,192,158.

(60) Provisional application No. 61/121,736, filed on Dec. 11, 2008.

(51) Int. Cl.
*A01N 25/30* (2006.01)
*A01N 57/20* (2006.01)

(52) U.S. Cl.
CPC ............. *A01N 25/30* (2013.01); *A01N 57/20* (2013.01)

(58) Field of Classification Search
None
See application file for complete search history.

(56) References Cited

U.S. PATENT DOCUMENTS

| | | |
|---|---|---|
| 5,668,085 A | 9/1997 | Forbes et al. |
| 5,703,015 A | 12/1997 | Berger et al. |
| 5,750,468 A | 5/1998 | Wright et al. |
| 6,451,735 B1 | 9/2002 | Ottaway et al. |
| RE37,866 E | 10/2002 | Wright et al. |
| 6,881,707 B2 | 4/2005 | Howat et al. |
| 7,049,270 B2 | 5/2006 | Lennon et al. |
| 9,192,158 B2 * | 11/2015 | Becher .................. A01N 25/30 |

FOREIGN PATENT DOCUMENTS

| | | |
|---|---|---|
| AU | 725067 | 10/2000 |
| AU | 774413 | 6/2004 |
| EP | 0472310 | 2/1992 |
| WO | 0105225 | 1/2001 |
| WO | 2005016002 | 2/2005 |
| WO | 2006034459 | 3/2006 |

OTHER PUBLICATIONS

Anonymous, "Aqueous Concentrate Pesticidal Compositions Having Reduced Eye Irritancy," 2001, Research Disclosure 446099, Mason Publications, 446/99, 1 page.
Invitation to Pay Additional Fees and Partial Search Report issued in PCT/US/23009/067485 dated Mar. 10, 2011, 8 pages.

* cited by examiner

*Primary Examiner* — Alton N Pryor
(74) *Attorney, Agent, or Firm* — Stinson Leonard Street LLP; Erin C. Robert

(57) ABSTRACT

The present invention generally relates to herbicidal compositions comprising a herbicide, an etheramine alkoxylate surfactant, an alkylamine alkoxylate surfactant having a high degree of alkoxylation and compatibilizer comprising, in some embodiments, an alkylamine alkoxylate surfactant having a low degree of alkoxylation or an alkylpolyglucoside surfactant. The herbicidal compositions are herbicidally efficacious and cause low eye irritation and low crop injury.

16 Claims, No Drawings

HERBICIDE FORMULATIONS CONTAINING AN ETHERAMINE AND ALKYLAMINE ALKOXYLATE SURFACTANT SYSTEM

REFERENCE TO RELATED APPLICATIONS

This application is a continuation of U.S. application Ser. No. 12/635,166, filed Dec. 10, 2009, which issued as U.S. Pat. No. 9,192,158 on Nov. 24, 2015 and which claims the benefit of U.S. provisional application Ser. No. 61/121,736, filed Dec. 11, 2008, the entire disclosure of which is incorporated herein by reference.

FIELD OF THE INVENTION

The present invention generally relates to herbicidal compositions having high weed efficacy, low eye irritation and low crop injury.

BACKGROUND OF THE INVENTION

Glyphosate is well known as a highly effective and commercially important herbicide useful for combating the presence of a wide variety of unwanted vegetation, including agricultural weeds. Glyphosate is conventionally applied as a formulated product dissolved in water to the foliage of annual and perennial grasses and broadleaf plants and the like, is taken up over a period of time into the leaves, and thereafter translocates throughout the plant.

Under most application conditions, the herbicidal efficacy of glyphosate can be significantly enhanced by including one or more surfactants in the composition to be applied. It is believed that such surfactants act partly by facilitating the penetration of glyphosate, a relatively hydrophilic compound, through the rather hydrophobic cuticle which normally covers the external above-ground surfaces of higher plants.

In some glyphosate formulations, certain glyphosate salts are preferred. For example, in some applications potassium glyphosate is preferred because it can be more highly loaded and is of lesser cost than many other glyphosate salts. However, potassium glyphosate is not highly compatible with some surfactants used in the art, such as tallowamines having from about 8 to about 25 ethoxy units.

It is known that potassium glyphosate shows good compatibility with etheramine alkoxylate surfactants of the formula:

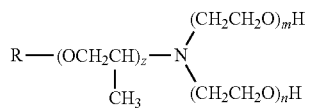

wherein R is $C_8$ to $C_{18}$, z is a number from 1 to 5 and m and n are average numbers such that m+n is in the range of from 2 to about 8. Commercial potassium glyphosate formulations typically contain up to about 135 g/L of such etheramines. Etheramine alkoxylate surfactants generally provide high herbicidal efficacy on weeds when formulated in compositions at concentrations in excess of about 120 grams per liter ("g/L"), but also may cause crop damage and eye irritation at that concentration. In particular, when formulated in excess of about 120 g/L, etheramines are generally placed in toxicity category II when tested according to the standard procedure prescribed in US Environmental Protection Agency (EPA) Publication 540/9-82-025, November 1982, entitled Pesticidal Assessment Guidelines, Subdivision F, Hazard Evaluation: Human and Domestic Animals, thereby indicating moderate eye irritation. In contrast, at low concentrations (such as about 65 g/L as described, for example, in U.S. Pat. No. 5,750,468 to Wright) etheramine alkoxylate surfactants are placed in toxicity category III indicating low irritancy to eyes. However, at such low surfactant concentrations herbicidal efficacy is not enhanced to the extent that it is in potassium glyphosate compositions containing significantly greater proportions of etheramine.

It is further known that glyphosate formulations containing etheramine alkoxylate surfactants can cause relatively greater crop injury to certain glyphosate tolerant plants such as Roundup Ready® corn, soybeans, canola or cotton as compared glyphosate formulations containing other surfactants known in the art.

A need exists for high efficacy etheramine-based herbicide compositions that are compatible with herbicides and salts thereof including the potassium salt, that cause little or no crop damage, and that have low eye irritancy and low toxicity.

SUMMARY OF THE INVENTION

The present invention provides efficacious herbicidal compositions comprising an alkylamine alkoxylate surfactant having a high degree of alkoxylation and an etheramine alkoxylate surfactant, the compositions having low toxicity and high biodegradability.

Briefly, one aspect of the present invention is directed to an aqueous herbicidal composition that is biologically effective to control growth of a susceptible plant, the composition comprising a water-soluble herbicide, a compatibilizer, and a surfactant component comprising an alkylamine alkoxylate surfactant and an etheramine alkoxylate surfactant. The alkylamine alkoxylate surfactant corresponds to the formula:

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

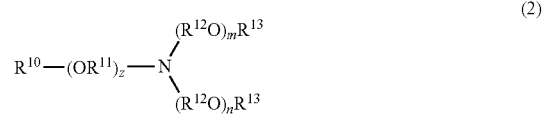

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60. The composition has a cloud point in excess of about 50° C.

Another aspect of the present invention is directed to an aqueous herbicidal composition that is biologically effective to control growth of a susceptible plant, the composition comprising a water-soluble herbicide, a surfactant component comprising an alkylamine alkoxylate surfactant and an etheramine alkoxylate surfactant, and a compatibilizer. The alkylamine alkoxylate surfactant corresponds to the formula:

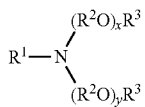  (1)

wherein $R^1$ is $C_{12-18}$ straight or branched chain hydrocarbyl, each $R^2$ is independently $C_{1-4}$, each $R^3$ is independently hydrogen or $C_{1-6}$ alkyl, and x+y is an average number of from about 5 to about 25. The etheramine alkoxylate surfactant corresponds to the formula:

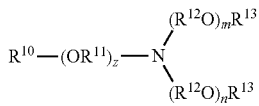  (2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that x+y is in the range of from 2 to about 60. The compatibilizer is of formula (3)

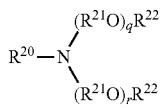  (3)

wherein $R^{20}$ is $C_{12-18}$ straight or branched chain hydrocarbyl, each $R^{21}$ is independently $C_{1-4}$ alkylene, each $R^{22}$ is independently hydrogen or $C_{1-6}$ alkyl, and q+r is an average number of from about 2 to about 4. The composition has a cloud point in excess of about 50° C.

Another aspect of the present invention is directed to an herbicidal composition that is biologically effective to control growth of a susceptible plant wherein the composition comprises a water-soluble herbicide comprising at least one organic amine salt of glyphosate, sodium glyphosate, trimethylsulfonium glyphosate, or mixtures thereof and a surfactant component comprising an alkylamine alkoxylate surfactant and an etheramine alkoxylate surfactant. The alkylamine alkoxylate surfactant corresponds to the formula:

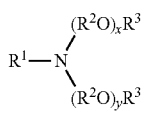  (1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

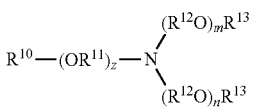  (2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Yet another aspect of the present invention is directed to an aqueous herbicidal concentrate composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

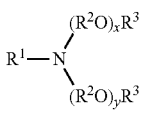  (1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

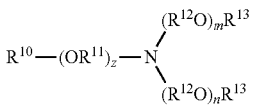  (2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60. The composition is an aqueous concentrate and the water-soluble herbicide concentration is at least 500 grams acid equivalent per liter.

Another aspect of the present invention is directed to an herbicidal composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

$$R^1\text{—}N\begin{array}{c}(R^2O)_xR^3\\ (R^2O)_yR^3\end{array} \quad (1)$$

wherein $R^1$ is $C_{12\text{-}18}$ straight or branched chain hydrocarbyl, each $R^2$ is independently $C_{1\text{-}4}$ alkylene, each $R^3$ is independently hydrogen or $C_{1\text{-}6}$ alkyl, and x+y is an average number of from about 5 to about 25. The etheramine alkoxylate surfactant corresponds to the formula:

$$R^{10}\text{—}(OR^{11})_z\text{—}N\begin{array}{c}(R^{12}O)_mR^{13}\\ (R^{12}O)_nR^{13}\end{array} \quad (2)$$

wherein $R^{10}$ is $C_{6\text{-}22}$ straight or branched chain hydrocarbyl, each $R^{11}$ is independently $C_{1\text{-}4}$ alkylene, each $R^{12}$ is independently $C_{1\text{-}4}$ alkylene, each $R^{13}$ is independently hydrogen or $C_{1\text{-}6}$ alkyl, z is an average number of from about 1 to about 10, m and n are average numbers such that m+n is in the range of from 2 to about 60. The weight ratio of the water-soluble herbicide on an acid equivalent basis to the surfactant component is from 3:1 to about 5:1.

Still another aspect of the present invention is directed to an herbicidal composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

$$R^1\text{—}N\begin{array}{c}(R^2O)_xR^3\\ (R^2O)_yR^3\end{array} \quad (1)$$

wherein $R^1$ is $C_{12\text{-}18}$ straight or branched chain hydrocarbyl, each $R^2$ is independently $C_{1\text{-}4}$ alkylene, each $R^3$ is independently hydrogen or $C_{1\text{-}6}$ alkyl, and x+y is an average number of from about 5 to about 25. The etheramine alkoxylate surfactant corresponds to the formula:

$$R^{10}\text{—}(OR^{11})_z\text{—}N\begin{array}{c}(R^{12}O)_mR^{13}\\ (R^{12}O)_nR^{13}\end{array} \quad (2)$$

wherein $R^{10}$ is $C_{6\text{-}22}$ straight or branched chain hydrocarbyl, each $R^{11}$ is independently $C_{1\text{-}4}$ alkylene, each $R^{12}$ is independently $C_{1\text{-}4}$ alkylene, each $R^{13}$ is independently hydrogen or $C_{1\text{-}6}$ alkyl, z is an average number of from about 1 to about 10, m and n are average numbers such that m+n is in the range of from 2 to about 60. The weight ratio of the etheramine alkoxylate surfactant to the alkylamine alkoxylate surfactant is from 70:30 to 50:50.

Still yet another aspect of the present invention is directed to an aqueous herbicidal concentrate composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

$$R^1\text{—}N\begin{array}{c}(R^2O)_xR^3\\ (R^2O)_yR^3\end{array} \quad (1)$$

wherein $R^1$ is $C_{12\text{-}18}$ straight or branched chain hydrocarbyl, each $R^2$ is independently $C_{1\text{-}4}$ alkylene, each $R^3$ is independently hydrogen or $C_{1\text{-}6}$ alkyl, and x+y is an average number of from about 5 to about 25. The etheramine alkoxylate surfactant corresponds to the formula:

$$R^{10}\text{—}(OR^{11})_z\text{—}N\begin{array}{c}(R^{12}O)_mR^{13}\\ (R^{12}O)_nR^{13}\end{array} \quad (2)$$

wherein $R^{10}$ is $C_{6\text{-}22}$ straight or branched chain hydrocarbyl, each $R^{11}$ is independently $C_{1\text{-}4}$ alkylene, each $R^{12}$ is independently $C_{1\text{-}4}$ alkylene, each $R^{13}$ is independently hydrogen or $C_{1\text{-}6}$ alkyl, z is an average number of from about 1 to about 10, m and n are average numbers such that m+n is in the range of from 2 to about 60. The composition has a density measured at 20° C. of from 1.33 to 1.4 grams per milliliter.

Yet another aspect of the present invention is directed to a solid herbicidal concentrate composition that, when dissolved and diluted, is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

$$R^1\text{—}N\begin{array}{c}(R^2O)_xR^3\\ (R^2O)_yR^3\end{array} \quad (1)$$

wherein $R^1$ is $C_{12\text{-}18}$ straight or branched chain hydrocarbyl, each $R^2$ is independently $C_{1\text{-}4}$ alkylene, each $R^3$ is independently hydrogen or $C_{1\text{-}6}$ alkyl, and x+y is an average number of from about 5 to about 25. The etheramine alkoxylate surfactant corresponds to the formula:

$$R^{10}\text{—}(OR^{11})_z\text{—}N\begin{array}{c}(R^{12}O)_mR^{13}\\ (R^{12}O)_nR^{13}\end{array} \quad (2)$$

wherein $R^{10}$ is $C_{6\text{-}22}$ straight or branched chain hydrocarbyl, each $R^{11}$ is independently $C_{1\text{-}4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Still another aspect of the present invention is directed to an herbicidal composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

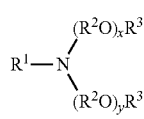

(1)

wherein $R^1$ is $C_{14-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

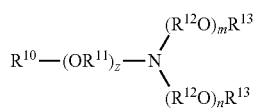

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Another aspect of the present invention is directed to an herbicidal composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

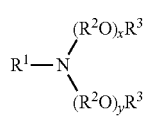

(1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of greater than 5. The etheramine alkoxylate surfactant corresponds to the formula:

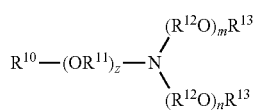

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Yet another aspect of the present invention is directed to an herbicidal composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

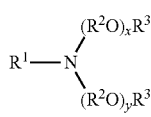

(1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

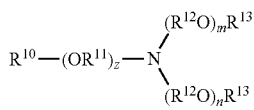

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60. The surfactant component further comprises a nonionic surfactant.

Yet another aspect of the present invention is directed to a solid herbicidal concentrate composition that is biologically effective to control growth of a susceptible plant, the composition comprising a water-soluble herbicide and a surfactant component comprising an alkylamine alkoxylate surfactant and an etheramine alkoxylate surfactant. The alkylamine alkoxylate surfactant corresponds to the formula:

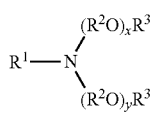

(1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

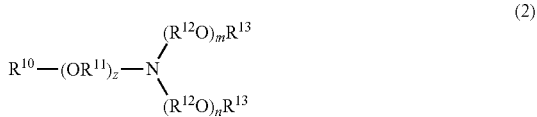

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Still another aspect of the present invention is directed to an aqueous herbicidal composition that is biologically effective to control growth of a susceptible plant, the composition comprising potassium glyphosate in combination with the isopropylamine salt of glyphosate, monoethanolamine salt of glyphosate, dimethylamine salt of glyphosate, or a mixture thereof. The composition further comprises a surfactant component comprising an alkylamine alkoxylate surfactant and an etheramine alkoxylate surfactant wherein the alkylamine alkoxylate surfactant corresponds to the formula:

(1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25, and wherein the etheramine alkoxylate surfactant corresponds to the formula:

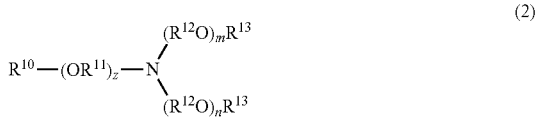

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60.

Still another aspect of the present invention is directed to an aqueous herbicidal composition that is biologically effective to control growth of a susceptible plant, the composition comprising potassium glyphosate and a surfactant component comprising an alkylamine alkoxylate surfactant and an etheramine alkoxylate surfactant wherein the alkylamine alkoxylate surfactant corresponds to the formula:

(1)

wherein $R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25. The etheramine alkoxylate surfactant corresponds to the formula:

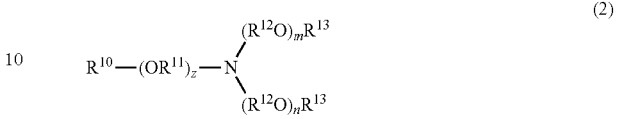

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to 4.

Still another aspect of the present invention is directed to an aqueous herbicidal composition that is biologically effective to control growth of a susceptible plant, the composition comprising potassium glyphosate and a surfactant component comprising a first etheramine alkoxylate surfactant corresponding to the formula:

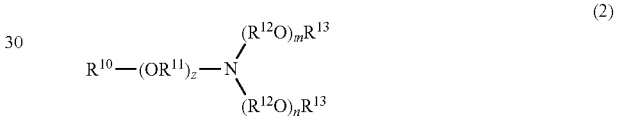

(2)

wherein, $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 5 to 8. The second etheramine alkoxylate surfactant is of formula (2) wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to 4.

Still another aspect of the present invention is directed to an herbicidal method comprising forming an application mixture by diluting any one of the aqueous compositions of the present invention with water and applying the application mixture to the foliage of a plant or plants.

Yet another aspect of the present invention is directed to an herbicidal method comprising forming an application mixture by dissolving a solid composition of any one of solid concentrated compositions of the present invention in water and applying the application mixture to the foliage of a plant or plants.

Other objects and features will be in part apparent and in part pointed out hereinafter.

DESCRIPTION OF THE PREFERRED EMBODIMENTS

The present invention is generally directed to an herbicidal surfactant system comprising an alkylamine alkoxylate surfactant having a high degree of alkoxylation and an etheramine alkoxylate surfactant. The herbicidal surfactant system can optionally further comprise a compatibilizer.

In accordance with the present invention, it has been discovered that the irritation and crop injury problems associated with herbicidal formulations containing a surfactant system comprising etheramine alkoxylate surfactants can be reduced by substituting a portion of the etheramine alkoxylate surfactant with an alkylamine alkoxylate surfactant having a high degree of alkoxylation. Surprisingly, the surfactant mixtures provide herbicidal efficacy comparable to highly efficacious etheramine alkoxylate surfactants despite the addition of the alkylamine alkoxylate surfactants which are known to provide comparably less efficacy in herbicidal compositions.

In accordance with the present invention, it has been further been discovered that potassium glyphosate, which is not highly compatible with a surfactant system comprising a combination of an alkylamine alkoxylate surfactant having a high degree of alkoxylation, for example, from about 8 to about 25 oxyalkylene units per molecule, and etheramine alkoxylate surfactant having, for example, from about 5 to about 15 oxyalkylene units per molecule, can be compatibilized with that surfactant system by an alkylamine alkoxylate surfactant having a low degree of alkoxylation or an alkylpolyglucoside ("APG") surfactant.

As used herein, a compatibilizer is a compound that improves the ability of an aqueous mixture comprising one or more herbicides, such as glyphosate salts, and one or more surfactants to exist in a single stable liquid phase and resist phase separation upon standing for an indefinite period of time.

Although reference is herein made to the herbicide glyphosate, one skilled in the art will understand that the principles of the present invention apply to herbicides in general, and the invention is not limited to glyphosate herbicidal compositions.

The term glyphosate comprises glyphosate acid and/or a derivative thereof. Derivatives include salts, esters, or compounds which are converted to glyphosate in plant tissues or which otherwise provide glyphosate anions. Glyphosate is an organic compound that at neutral pH contains three acidic protonatable groups, and in its acid form is relatively insoluble in water. Therefore, glyphosate is normally formulated and applied to plants as a water-soluble salt formed from glyphosate acid and a counterion, for example, potassium ($K^+$), isopropylamine ($IPA^+$), ammonium ($NH_4^+$), or other suitable counterions known in the art such as those described below. Although monobasic, dibasic, and tribasic salts of glyphosate can be made, it has generally been preferred to formulate and apply glyphosate substantially in the form of a monobasic salt, for example, as a mono-(organic ammonium) salt such as the mono IPA salt or the mono K salt, or as either monobasic or dibasic ammonium ($NH_4$) salt. Other suitable glyphosate salts include sodium (Na), monoethanolamine (MEA), diethanolamine (DEA), triethanolamine (TEA), trimesium (TMS), n-propylamine, methylamine, ethylamine, hexamethylenediamine, dimethylamine (DMA), and mixtures thereof. In dry formulations, the monoammonium and sodium salts, or mixtures thereof, are preferred. The monobasic salt formulations can vary modestly from an exact 1:1 countercation to glyphosate ratio, while the ammonium salts can comprise a ratio of $NH_4^+$ ion to glyphosate of 1:1 to 1.8:1. Typically, the aqueous glyphosate salt formulations of the present invention have a pH of from about 4 to about 7. Within those pH ranges, glyphosate salt predominantly disassociates to form glyphosate anions and counterions. In some other embodiments, glyphosate can be present in the form of an agriculturally acceptable ester (for instance, methyl, ethyl, ethoxyethyl, or branched or straight chain propyl, butyl, octyl, butoxyethyl or methoxypropyl). The term "agronomically acceptable" includes glyphosate derivatives that allow agriculturally and economically useful herbicidal activity of a glyphosate anion in residential or industrial applications.

It has yet been further discovered that compatible compositions can be formed from a surfactant system comprising an alkylamine alkoxylate surfactant having a high degree of alkoxylation, for example, from about 8 to about 25 oxyalkylene units per molecule, and etheramine alkoxylate surfactant having, for example, from about 5 to about 15 oxyalkylene units per molecule, and the potassium salt of glyphosate by including one or more of the isopropylamine ("IPA") salt of glyphosate, the monoethanolamine salt of glyphosate, or the dimethylamine salt of glyphosate.

Based on experimental evidence to date, it has been discovered that herbicidal compositions containing surfactant blends of the present invention comprising an etheramine alkoxylate surfactant in combination with an alkylamine alkoxylate surfactant having a high degree of alkoxylation and an alkylamine alkoxylate compatibilizing surfactant having a low degree of alkoxylation can provide (i) enhanced efficacy and (ii) reduced injury to glyphosate-tolerant crops as compared to either of two reference compositions, each of which has the same concentration of the same water-soluble herbicide, e.g., a glyphosate salt such as K glyphosate or IPA glyphosate, the same total surfactant concentration, and the same concentration of any other adjuvants that may be present in the formulation. The first reference composition comprises a combination of the herbicide and a surfactant component containing only the etheramine alkoxylate surfactant and the second reference composition comprises the herbicide and a surfactant component containing only the combination of the alkylamine alkoxylate surfactants having high and low degrees of alkoxylation. It has yet been further discovered that, at constant total surfactant content, injury to glyphosate tolerant plants decreases as the etheramine alkoxylate surfactant content in the formulation decreases.

It has further been discovered that the compositions of the present invention are practically non-toxic, are essentially non-irritating to skin and are only moderately irritating to eyes. In particular, when measured according to the methods provided in U.S. Environmental Protection Agency Office of Prevention, Pesticides and Toxic Substances, Health Effects Test Guidelines (for example, OPPTS 870.2400 Acute Eye Irritation, August 1998; OPPTS 870.2500 Acute Dermal Irritation, August 1998; OPPTS 870.1100 Acute Oral Toxicity, December 2002; OPPTS 870.1200 Acute Dermal Toxicity, August 1998; OPPTS 870.1300 Acute Inhalation Toxicity, August 1998; and OPPTS 870.2600 Skin Sensitization, March 2003), the compositions of the present invention are generally classified in the categories indicated in the table below where FIFRA refers to "Federal Insecticide, Fungicide and Rodenticide Act" classification:

| Evaluation | Category | Description |
| --- | --- | --- |
| Acute oral toxicity (rat, $LD_{50}$) | FIFRA category IV | practically non-toxic |
| Acute dermal toxicity (rat, $LD_{50}$) | FIFRA category IV | practically non-toxic |

-continued

| Evaluation | Category | Description |
|---|---|---|
| Acute inhalation toxicity (rat, $LC_{50}$) | FIFRA category IV | practically non-toxic |
| Skin Irritation (rabbit) | FIFRA category IV | essentially non-irritating |
| Eye Irritation (rabbit) | FIFRA category III | moderate irritation |
| Skin Sensitization (guinea pig) | negative | |

Some embodiments of the present invention are directed to herbicidal compositions comprising an herbicide and a surfactant system comprising an alkylamine alkoxylate surfactant having a high degree of alkoxylation and an etheramine alkoxylate surfactant.

The alkylamine alkoxylate surfactant having a high degree of alkoxylation is of formula (1):

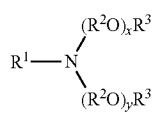

(1)

wherein $R^1$ is a straight or branched chain $C_{12}$ to $C_{18}$ hydrocarbyl group (e.g., tallow, soya, coco or oleyl), more preferably a mixture of straight or branched chain $C_{14}$ to $C_{18}$ hydrocarbyl groups, still more preferably a mixture of straight or branched chain $C_{16}$ to $C_{18}$ alkyl (tallow), $R^2$ is $C_1$ to $C_4$ alkylene, more preferably $C_2$, each $R^3$ is independently hydrogen or $C_1$ to $C_6$ alkyl, preferably hydrogen, and, in some embodiments, x and y are average numbers such that x+y is in the range of from about 5 to about 25, more preferably from about 5 to about 20, more preferably from about 8 to about 20, more preferably from 8 to about 15, and still more preferably from about 9 to about 10. In other embodiments, x and y are average numbers such that x+y is greater than 5, such as in the range of from 6 to about 15, from 6 to about 12, or from 6 to about 10. Examples of suitable surfactants include, without restriction, Berol 300 (cocoamine 5EO), Berol 381 (tallowamine 15EO), Berol 391 (tallowamine 5EO), Berol 397 (cocoamine 15 EO), Berol 398 (cocoamine 11 EO), Berol 498 (tallowamine 10 EO), Ethomeen C/15 (cocoamine 5EO), Ethomeen C/25 (cocoamine 15 EO), Ethomeen T/15 (tallowamine 5EO), Ethomeen T/20 (tallowamine 10EO), Ethomeen T/19 (tallowamine 9EO), Ethomeen T/25 (tallowamine 15 EO), Witcamine TAM-105 (tallowamine 10 EO), Witcamine TAM-80 (tallowamine 8 EO), Witcamine TAM-60 (tallowamine 6EO), all available from Akzo Nobel.

The etheramine alkoxylate surfactant is of formula (2):

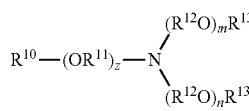

(2)

wherein $R^{10}$ is a straight or branched chain $C_6$ to $C_{22}$ hydrocarbyl group (e.g., tallow, soya, coco or oleyl), more preferably a mixture of straight or branched chain $C_{12}$ to $C_{18}$ alkyl, more preferably a mixture of straight or branched chain $C_{12}$ to $C_{16}$ alkyl, more preferably a mixture of straight or branched chain $C_{12}$ to $C_{14}$ alkyl, $R^{11}$ is $C_1$ to $C_4$ alkylene, more preferably $C_3$ alkylene, z is an average number of from 1 to about 10, more preferably from about 1 to about 5, and still more preferably about 2, $R^{12}$ is $C_1$ to $C_4$ alkylene, more preferably $C_2$, m and n are average numbers such that m+n is in the range of from about 2 to about 60, preferably from about 2 to about 20, from about 5 to about 15, from about 2 to about 10, from about 5 to about 10, from about 5 to about 8, more preferably about 5, and each $R^{13}$ is independently hydrogen or $C_1$ to $C_6$ alkyl, preferably hydrogen. When combined with the water soluble herbicide potassium glyphosate, m and n are average numbers such that m+n is in the range of from about 5 to about 8 is preferred. Examples of suitable surfactants include, without restriction, Tomamine E-14-2 (bis-(2-hydroxyethyl)isodecyloxypropylamine), Tomamine E-14-5 (poly-(5) oxyethylene isodecyloxypropylamine), Tomamine E-17-2 (bis-(2-hydroxyethyl) isotridecyloxypropylamine), Tomamine E-17-5 (poly (5) oxyethylene isotridecyloxypropylamine), Tomamine E-19-2 (bis-(2-hydroxyethyl)linear alkyloxypropylamine) all available from Air Products, and Surfonic AGM-550 (where $R^{10}$ is $C_{12-14}$, $R^{11}$ is isopropyl, $R^{12}$ is $C_2$ and the sum of m and n is 5) available from Huntsman.

The weight ratio of the etheramine alkoxylate surfactant to the alkylamine alkoxylate surfactant having a high degree of alkoxylation is from about 90:10 to about 10:90, preferably from about 80:20 to about 40:60, more preferably from about 80:20 to about 50:50. In some preferred embodiments, the ratio is not greater than about 70:30, for example from about 70:30 to about 50:50. The weight ratio of glyphosate a.e. to total surfactant of from about 1:1 to about 6:1, preferably from about 3:1 to about 5:1, more preferably from about 4:1 to about 4.5:1. The preferred ratios are generally based on a balance between optimum biological and cost performance. With less etheramine surfactant a loss of weed control begins to be observed and with more the increase in weed control does not offset the additional cost of the formulation.

Other embodiments of the present invention are directed to compositions comprising the etheramine alkoxylate surfactant and the alkylamine alkoxylate surfactant described above, and a compatibilizer. The compatibilizer can be an alkylamine alkoxylate surfactant having a low degree of alkoxylation or an alkylpolyglucoside ("APG") surfactant.

Still other embodiments of the present invention are directed to compatible compositions comprising the etheramine alkoxylate surfactant and the alkylamine alkoxylate surfactant described above and potassium glyphosate salt in combination with one or more of the IPA salt of glyphosate, the MEA salt of glyphosate, or the DMA salt of glyphosate.

Yet other embodiments of the present invention are directed to compatible compositions comprising the etheramine alkoxylate surfactant and the alkylamine alkoxylate surfactant described above, and one or more of the IPA salt of glyphosate, the MEA salt of glyphosate, or the DMA salt of glyphosate.

When the compatibilizer is an alkylamine alkoxylate surfactant having a low degree of alkoxylation, it is of formula (3):

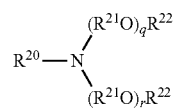

(3)

$R^{20}$ is preferably a straight or branched chain $C_{12}$ to $C_{18}$ hydrocarbyl group (e.g., tallow, soya, coco or oleyl), more preferably a mixture of straight or branched chain $C_{12}$ to $C_{14}$ alkyl (coco), most preferably $C_{12}$, $R^{21}$ is preferably $C_1$ to $C_4$ alkylene, more preferably $C_2$, q and r are preferably average numbers such that q+r is in the range of from 2 to about 6, more preferably from about 2 to about 4, more preferably about 2, and each $R^{22}$ is independently hydrogen or $C_1$ to $C_6$ alkyl, preferably hydrogen. Examples of suitable surfactants include, without restriction, Witcamine 302 (cocoamine 2EO), Berol 307 (cocoamine 2EO), Ethomeen C/12 (cocoamine 2EO), Ethomeen S/12 (soyamine 2EO) and Ethomeen T/12 (tallowamine 2EO), all available from Akzo Nobel.

When the compatibilizer is an APG surfactant, it is of formula (4):

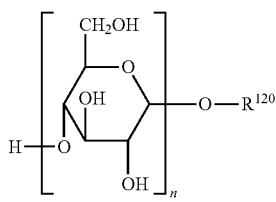

(4)

wherein n is the degree of polymerization, or number of glucose groups, expressed as an average number. $R^{120}$ is a branched or straight chain hydrocarbyl, more preferably an alkyl group, preferably having from 4 to 18 carbon atoms or a mixture of alkyl groups having an average value within the given range. Preferably n is an average number between 1 and about 5, and more preferably between 1 and about 3. Typical of alkylglucosides is the product commercially available under the trade names AL2042 (Imperial Chemical Industries PLC) wherein n is an average of 1.7 and R is a mixture of octyl (45%) and decyl (55%), the product commercially available under the trade name AGRIMUL PG2069 (Henkel Corp) wherein n is an average of 1.6 and R is a mixture of nonyl (20%), decyl (40%) and undecyl (40%), and the product commercially available under the trade name BEROL AG6202 (Akzo Nobel) which is 2-ethyl-1-hexylglycoside.

In embodiments where a compatibilizer surfactant is used, it has been discovered that stable glyphosate salt concentrate compositions can be prepared when the weight ratio range of the alkylamine alkoxylate surfactant having a high degree of alkoxylation to the compatibilizer surfactant is from about 80:20 to about 50:50, from about 65:35 to about 50:50, preferably about 55:45. In embodiments where the water soluble herbicide is potassium glyphosate, the preferred weight ratio range is about 65:35 to about 50:50, more preferably about 55:45. In embodiments where the water soluble herbicide is a glyphosate salt other than the potassium salt, for example, the IPA, DMA or MEA salt, the preferred weight ratio range is from about 80:20 to about 50:50, more preferably from about 65:35 to about 60:40. The weight ratio range of the etheramine alkoxylate surfactant to the sum of the alkylamine alkoxylate surfactant and compatibilizer surfactant is from about 90:10 to about 10:90, preferably from about 80:20 to about 40:60, more preferably from about 80:20 to about 50:50, still more preferably from about 70:30 to about 50:50. In such embodiments, the weight ratio of glyphosate acid equivalent ("a.e.") to total surfactant is from about 1:1 to about 6:1, preferably from about 3:1 to about 5:1, more preferably from about 4:1 to about 4.5:1.

In the case of potassium glyphosate, it has been discovered that the etheramine alkoxylate surfactants having a low degree of alkoxylation, such as from 2 to 4 oxyalkylene units, will compatibilize potassium glyphosate and the alkylamine alkoxylate surfactant to some extent. In some embodiments, the surfactant system comprises the etheramine surfactant having a low degree of alkoxylation and the alkylamine alkoxylate surfactant in a weight ratio of etheramine to alkylamine alkoxylate of from about 80:20 to about 50:50, more preferably from about 70:30 to about 50:50. In other embodiments, the surfactant system comprises the etheramine surfactant having a low degree of alkoxylation, and an etheramine surfactant having a higher degree of alkoxylation, such as from about 5 to about 8 oxyalkylene units, and alkylamine alkoxylate surfactant wherein the weight ratio of the etheramine surfactant having a higher degree of alkoxylation to the sum of the alkylamine alkoxylate and etheramine having a low degree of alkoxylation is from about 65:35 to about 50:50.

When the herbicide comprises a mixture of the potassium salt of glyphosate and one or more of the IPA salt of glyphosate, the MEA salt of glyphosate, the DMA salt of glyphosate, or a mixture thereof, a mole ratio of potassium glyphosate a.e. to sum of the other glyphosate salts (on an a.e. basis) is typically from about 90:10 to about 10:90, preferably from about 90:10 to about 50:50, more preferably from about 80:20 to about 60:40. The weight ratio of the etheramine alkoxylate surfactant to the alkylamine alkoxylate surfactant, the weight ratio of glyphosate a.e. to total surfactant, and glyphosate concentration are as described above. If a compatibilizer surfactant is present, the weight ratio of the alkylamine alkoxylate surfactant to the compatibilizer surfactant and weight the ratio of the etheramine alkoxylate surfactant to the sum of the alkylamine alkoxylate surfactant to the compatibilizer surfactant are as described above.

The glyphosate compositions of the present inventions can be in the form of a tank mix (also termed an "application mixture"), a liquid concentrate or a solid concentrate. Tank mix glyphosate concentrations can be from about 0.001 weight percent acid equivalent ("wt % a.e.") to about 5 wt % a.e., or about 0.1 to about 50 g a.e./L, from about 0.1 to about 20 g a.e./L, from 0.5 to 20 g a.e./L, from about 0.5 to about 10 g a.e./L or even from about 0.5 to about 5 g a.e./L. Liquid concentrate concentrations range from about 5 wt % a.e. to about 50 wt % a.e., for example 5, 10, 15, 20, 25, 30, 35, 40, 45 or even 50 wt % a.e. Expressed on an alternative basis, the glyphosate concentration in liquid glyphosate concentrate compositions can be about 50 grams acid equivalent per liter ("g a.e./L") to about 600 g a.e./L, for example 360, 400, 500, 540 or 600 g a.e./L. The density of the glyphosate formulations of the present invention is typically at least 1.18 grams per milliliter ("g/mL"), such as, for example, 1.21, 1.25, 1.3, 1.35, 1.4 or even 1.45 g/mL. Solid (or dry) compositions typically have a glyphosate concentration of from about 20 wt % a.e. to about 80 wt % a.e. Compatibilizers, such as a compatibilizing surfactant, are typically not required in solid compositions.

In some advantageous embodiments of the present invention, aqueous concentrate compositions that contain at least 500 g a.e./L glyphosate preferably have a viscosity (Haake viscosity) of less than 30 centipoise ("cPs") at 25° C., less than 60 cPs at 15° C., less than 105 cPs at 10° C., or even less than 110 cPs at 5° C.

Spray solutions of the present invention may be prepared on site by the ultimate consumer shortly before application to the foliage of vegetation or weeds to be eliminated or controlled by diluting the aqueous concentrate herbicidal formulations, or by dissolving or dispersing solid particles containing glyphosate. Alternatively, herbicidal formulations of the present invention may be supplied to the ultimate consumer on a "ready to use" basis.

The herbicidal formulations of the present invention may optionally contain one or more additional surfactants, one or more additional herbicides, and/or other adjuvants or ingredients.

In some embodiments, a di-carboxylic acid compound such as, for example, oxalic acid, malonic acid, succinic acid, glutaric acid, maleic acid, adipic acid, and fumaric acid, or a salt, ester thereof or mixtures thereof can be added to the compositions of the present invention. Oxalic acid and salts thereof are preferred. The addition of a relatively small amount of oxalic acid significantly reduces the amount of surfactant needed to provide a stable composition which, upon dilution and application to foliage of a plant, provides desired plant growth control. It also significantly improves the performance of many surfactants which otherwise provide poor growth control, enabling the use of a broader range of surfactants in herbicidal formulations. Typically, in liquid systems of the present invention, the weight ratio of total surfactant to dicarboxylic acid compound may be from about 1:1 to about 50:1, more preferably 5:1 to 40:1 and most preferably from about 5:1 to about 20:1. It is believed that this ratio of total surfactant to dicarboxylic acid would significantly enhance the herbicidal performance of the resulting formulation. In dry formulations, the weight ratio of total surfactant to dicarboxylic acid compound is between about 50:1 and about 1:30, more preferably between about 1:1 and about 5:1, and most preferably between about 1:1 and about 3:1. Preferably, the weight ratio of glyphosate a.e. to dicarboxylic acid is between about 1:1 and about 500:1, more preferably about 2:1 to about 100:1, and most preferably between about 2:1 to about 50:1 in liquid and dry formulations.

In other embodiments, compositions of the present invention can be combined with a fatty acid component selected from caprylic acid ($C_8$), pelargonic acid ($C_9$), capric acid ($C_{10}$), undecanoic acid ($C_{11}$), lauric acid ($C_{12}$), palmitic acid ($C_{16}$), stearic acid, oleic acid, linoleic acid and linolenic (all $C_{18}$), their salts and mixtures thereof. Pelargonic acid and salts thereof are generally preferred. A weight ratio range of glyphosate a.e. to fatty acid of from about 20:1 to about 1:50, from about 5:1 to about 1:5 or event from about 2:1 to 1:2 is preferred. Such compositions may further comprise an inorganic ammonium salt, for example ammonium sulfate, at a ratio of glyphosate a.e. to ammonium salt of from about 10:1 to about 1:10, from about 5:1 to about 1:5 or even from about 2:1 to about 1:2. In some embodiments, the compositions comprise from about 0.1% to about 5% by weight (a.e.) glyphosate, from about 0.25% to about 5% fatty acid and optionally comprise from about 0.5% to about 4% by weight inorganic ammonium salt.

A foam moderating amount of various antifoam agents can be added to the compositions of the present invention to reduce the foaming generated during dilution, mixing and spraying operations. Examples of suitable antifoams include silicone compounds, long-chain alcohols, monocarboxylic fatty acids and salts thereof, high molecular weight fatty esters. Silicone compounds generally contain siloxane units and hydrocarbyl groups, for example, polydimethylsiloxanes having timethylsilyl end blocking units and dimethylpolysiloxane. Alcohols include octanol (e.g., 2-octanol) and decanol (e.g., 1-decanol). Monocarboxylic fatty acids and their salts typically have hydrocarbyl chains of 10 to 24 carbon atoms. Suitable salts include the alkali metal salts such as sodium, potassium and lithium, and ammonium and alkanolammonium salts. High molecular weight fatty esters include, for example, fatty acid esters of monovalent alcohols, aliphatic $C_{18\text{-}40}$ ketones and N-alkylated amino triazines. A weight ratio of antifoam to surfactant from 1:100 to 1:1000 is generally preferred.

Additional cosurfactants can be optionally included in the formulations of the present invention. Such cosurfactants include, for example, nonionic, anionic and amphoteric surfactants as described below and mixtures thereof, wherein the surfactant component is present in an amount sufficient to enhance pesticidal efficacy while maintaining the desired toxicology and biodegradability characteristics. Generally, in liquid compositions of the present invention, the additional surfactant comprises no more than about 20%, no more than 10% or even no more than 5% by weight, or ranges thereof (for instance, 5% to 20% or 5% to 10%), of the total surfactant content. In solid compositions of the present invention, the additional surfactant can comprise 5%, 10%, 20%, 30%, 40% or even 50% by weight, or ranges thereof (for instance, 5% to 20% or 10% to 50%) of the total surfactant content.

Cationic cosurfactants include:

(a) a secondary or tertiary amine having the formula:

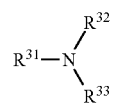

(5)

wherein $R^{31}$ is hydrocarbyl having from 1 to about 30 carbon atoms, and $R^{32}$ and $R^{33}$ are hydrogen or hydrocarbyl having from 1 to about 30 carbon atoms. In this context, preferred $R^{31}$, $R^{32}$, and $R^{33}$ hydrocarbyl groups are linear or branched alkyl, linear or branched alkenyl, linear or branched alkynyl, aryl, or aralkyl groups. Preferably, $R^{31}$ is a linear or branched alkyl or linear or branched alkenyl group having from about 8 to about 30 carbon atoms, and $R^{32}$ and $R^{33}$ are independently hydrogen or a linear or branched alkyl or linear or branched alkenyl group having from 1 to about 6 carbon atoms. More preferably, $R^{31}$ is a linear or branched alkyl or alkenyl group having from about 12 to about 22 carbon atoms, and $R^{32}$ and $R^{33}$ are independently hydrogen, methyl or ethyl. In one embodiment of the amine of formula (1), $R^{31}$ is a linear or branched alkyl group having from about 12 to about 22 carbon atoms, and $R^{32}$ and $R^{33}$ are independently linear or branched hydroxyalkyl groups having from 1 to about 6 carbon atoms;

(b) quaternary ammonium salts having the formula:

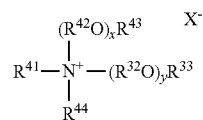

(6)

wherein $R^{41}$ is hydrocarbyl or substituted hydrocarbyl having from 1 to about 30 carbon atoms, $R^{42}$ in each of the $(R^{42}O)_x$ and $(R^{42}O)_y$ groups is independently $C_2$-$C_4$ alkylene, $R^{43}$ is hydrogen, or a linear or branched alkyl group having from 1 to about 4 carbon atoms, $R^{44}$ is hydrocarbyl or substituted hydrocarbyl having from 1 to about 30 carbon atoms, x and y are independently an average number from 1 to about 40, and $X^-$ is an agriculturally acceptable anion such as chloride, bromide, iodide, sulfate, ethyl sulfate, phosphate, acetate, propionate, lactate, citrate or tartrate or glyphosate. In this context, preferred $R^{41}$ and $R^{44}$ hydrocarbyl groups are linear or branched alkyl, linear or branched alkenyl, linear or branched alkynyl, aryl, or aralkyl groups. Preferably, $R^{41}$ and $R^{44}$ are independently a linear or branched alkyl or linear or branched alkenyl group having from 1 to about 25 carbon atoms, $R^{42}$ in each of the $(R^{42}O)_x$ and $(R^{42}O)_y$ groups is independently $C_2$-$C_4$ alkylene, $R^{43}$ is hydrogen, methyl or ethyl, and the sum of x and y is an average number from about 2 to about 30. More preferably, $R^{41}$ and $R^{44}$ are independently a linear or branched alkyl group having from 1 to about 22 carbon atoms, $R^{42}$ in each of the $(R^{42}O)_x$ and $(R^{42}O)_y$ groups is independently ethylene or propylene, $R^{43}$ is hydrogen or methyl, and the sum of x and y is an average number from about 2 to about 20. Even more preferably, $R^{41}$ is a linear or branched alkyl group having from about 8 to about 22 carbon atoms and $R^{44}$ is a linear or branched alkyl group having from 1 to about 22 carbon atoms, $R^{42}$ in each of the $(R^{42}O)_x$ and $(R^{42}O)_y$ groups is independently ethylene or propylene, $R^{43}$ is hydrogen or methyl, and x is an average number from about 2 to about 20. Most preferably, $R^{41}$ is a linear or branched alkyl group having from about 8 to about 22 carbon atoms and $R^{44}$ is a linear or branched alkyl group having from 1 to about 6 carbon atoms, $R^{42}$ in each of the $(R^{42}O)_x$ and $(R^{42}O)_y$ groups is independently ethylene or propylene, $R^{43}$ is hydrogen or methyl, and x is an average number from about 2 to about 15, or $R^{41}$ and $R^{44}$ are independently a linear or branched alkyl group having from about 8 to about 22 carbon atoms, $R^{42}$ in each of the $(R^{42}O)_x$ and $(R^{42}O)_y$ groups is independently ethylene or propylene, $R^{43}$ is hydrogen or methyl, and x is an average number from about 5 to about 15. Preferred dialkoxylated tertiary amines include Trymeen™ 6617 (from Cognis) and Ethomeen™ C/12, C/15, C/20, C/25, T/12, T/15, T/20 and T/25 (from Akzo Nobel. Examples of dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide;

(c) monoalkoxylated tertiary amines and quaternary ammonium salts having the formulae:

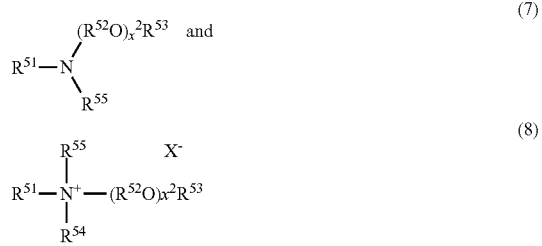

(7)

(8)

wherein $R^{51}$ and $R^{55}$ are independently hydrogen or hydrocarbyl or substituted hydrocarbyl having from 1 to about 30 carbon atoms, $R^{54}$ is hydrocarbyl or substituted hydrocarbyl having from 1 to about 30 carbon atoms, $R^{52}$ in each of the $(R^{52}O)_x^2$ groups is independently $C_2$-$C_4$ alkylene, $R^{53}$ is hydrogen, or a linear or branched alkyl group having from 1 to about 30 carbon atoms, $x^2$ is an average number from 1 to about 60, and $X^-$ is an agriculturally acceptable anion as described above. In this context, preferred $R^{51}$, $R^{54}$, and $R^{55}$ hydrocarbyl groups are linear or branched alkyl, linear or branched alkenyl, linear or branched alkynyl, aryl, or aralkyl groups. Preferably, $R^{51}$, $R^{54}$ and $R^{55}$ are independently a linear or branched alkyl or linear or branched alkenyl group having from 1 to about 25 carbon atoms, $R^{52}$ in each of the $(R^{52}O)_x^2$ groups is independently $C_2$-$C_4$ alkylene, $R^{53}$ is hydrogen, methyl or ethyl, and $x^2$ is an average number from 1 to about 40. More preferably, $R^{51}$, $R^{54}$ and $R^{55}$ are independently a linear or branched alkyl group having from 1 to about 22 carbon atoms, $R^{52}$ in each of the $(R^{52}O)_x^2$ groups is independently ethylene or propylene, $R^{53}$ is hydrogen or methyl, and $x^2$ is an average number from 1 to about 30. Even more preferably, $R^{51}$ is a linear or branched alkyl group having from about 8 to about 22 carbon atoms, $R^{52}$ in each of the $(R^{52}O)_x^2$ groups is independently ethylene or propylene, $R^{53}$ is hydrogen or methyl, $R^{54}$ and $R^{55}$ are independently a linear or branched alkyl group having from 1 to about 22 carbon atoms, and $x^2$ is an average number from 1 to about 30. Even more preferably, $R^{51}$ is a linear or branched alkyl group having from about 8 to about 22 carbon atoms, $R^{52}$ in each of the $(R^{52}O)_x^2$ groups is independently ethylene or propylene, $R^{53}$ is hydrogen or methyl, $R^{54}$ and $R^{55}$ are independently a linear or branched alkyl group having from 1 to about 6 carbon atoms, and $x^2$ is an average number from about 5 to about 25. Most preferably, $R^{51}$ is a linear or branched alkyl group having from about 16 to about 22 carbon atoms, $R^{52}$ in each of the $(R^{52}O)_x^2$ groups is independently ethylene or propylene, $R^{53}$ is hydrogen or methyl, $R^{54}$ and $R^{55}$ are independently a linear or branched alkyl group having from 1 to about 3 carbon atoms, and $x^2$ is an average number from about 5 to about 25. Examples of monoalkoxylated quaternary ammonium surfactants include PEG 7 $C_{18}$ dimethyl ammonium chloride and PEG 22 $C_{18}$ dimethyl ammonium chloride;

(d) quaternary ammonium salts having the formula:

(9)

wherein $R^{61}$, $R^{63}$ and $R^{64}$ are independently hydrogen or hydrocarbyl or substituted hydrocarbyl having from 1 to about 30 carbon atoms, $R^{62}$ is hydrocarbyl or substituted hydrocarbyl having from 1 to about 30 carbon atoms, and $X^-$ is an agriculturally acceptable anion. In this context, preferred $R^{61}$, $R^{62}$, $R^{63}$, and $R^{64}$ hydrocarbyl groups are linear or branched alkyl, linear or branched alkenyl, linear or branched alkynyl, aryl, or aralkyl groups. Preferably, $R^{61}$ is a linear or branched alkyl or linear or branched alkenyl group having from about 8 to about 30 carbon atoms, and $R^{62}$, $R^{63}$ and $R^{64}$ are independently a linear or branched alkyl or linear or branched alkenyl group having from 1 to about 30 carbon atoms. More preferably, $R^{61}$ is a linear or branched alkyl or linear or branched alkenyl group having from about 8 to about 22 carbon atoms, and $R^{62}$, $R^{63}$ and $R^{64}$ are independently a linear or branched alkyl or linear or branched alkenyl group having from 1 to about 6 carbon atoms. Even more preferably, $R^{61}$ is a linear or branched alkyl group having from about 8 to about 16 carbon atoms, and $R^{62}$, $R^{63}$ and $R^{64}$ are independently a linear or branched alkyl group having from 1 to about 6 carbon atoms. Most preferably, $R^{61}$ is a linear or branched alkyl group having from about 8 to about 14 carbon atoms, and $R^{62}$, $R^{63}$ and $R^{64}$ are methyl. Examples of quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

Anionic cosurfactants include, without restriction, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, $C_{8-20}$ alkyl polyoxyethylene sulfosuccinates and sulfosuccinamates, and $C_{8-20}$ acyl glutamates, sarcosinates, isothionates and taurates.

Alkyl alkoxylated phosphates have the formulae:

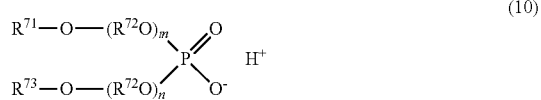

(10)

wherein $R^{71}$ and $R^{73}$ are independently a linear or branched alkyl, linear or branched alkenyl, linear or branched alkynyl, aryl, or aralkyl group having from about 4 to about 30 carbon atoms; $R^{72}$ in each of the $(R^{72}O)_m$ and the n $(R^{72}O)$ groups is independently $C_2$-$C_4$ alkylene; and m and n are independently from 1 to about 30; and

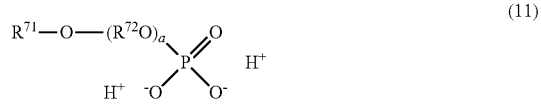

(11)

wherein $R^{71}$ is a linear or branched alkyl, linear or branched alkenyl, linear or branched alkynyl, aryl, or aralkyl group having from about 8 to about 30 carbon atoms; $R^{72}$ in each of the $(R^{72}O)_a$ groups is independently $C_2$-$C_4$ alkylene; and a is from 1 to about 30. Representative alkyl alkoxylated phosphates include oleth-10 phosphate, oleth-20 phosphate and oleth-25 phosphate.

Nonionic cosurfactants include, without restriction, polysiloxanes, polyoxyalkylene primary and secondary $C_{8-20}$ alkylethers, alkoxylated acetylenic diols, polyoxyalkylene mono- and di($C_{8-20}$ alkyl)phenylethers, polyoxyalkylene di- and tristyrylphenylethers, polyoxyalkylene $C_{8-20}$ fatty acid esters, polyoxyalkylene $C_{8-20}$ alcohols, alkoxylated vegetable oils, block copolymers of ethylene oxide and propylene oxide and $C_{2-6}$ alkyl adducts thereof, glycerol fatty acid esters, sorbitan $C_{8-20}$ mono-, di- and tri($C_{8-20}$ fatty acid) esters, polyoxyalkylene sorbitan mono-, di- and tri($C_{8-20}$ fatty acid) esters and sucrose esters.

Polysiloxanes have the formula:

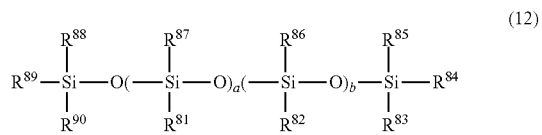

(12)

wherein $R^{81}$ is $-C_nH_{2n}O(CH_2CH_2O)_m(CH_2CH(CH_3)O)_q$ X, n is 0 to 6, a is 0 to about 100, b is 0 to about 10, m is 0 to about 30, q is 0 to about 30, X is hydrogen or a $C_{1-20}$ hydrocarbyl or $C_{2-6}$ acyl group, and the $R^{82}$, $R^{83}$, $R^{84}$, $R^{85}$, $R^{86}$, $R^{87}$, $R^{88}$, $R^{89}$, $R^{90}$ groups are independently substituted or unsubstituted $C_{1-20}$ hydrocarbyl or nitrogen containing groups. Generally, in preferred embodiments, n is 0 to 6, a is 1 to about 30, b is 0 to about 10, m is 0 to about 30, q is 0 to about 3, X is hydrogen or a $C_{1-6}$ hydrocarbyl or $C_{2-6}$ acyl group, and the $R^{82}$, $R^{83}$, $R^{84}$, $R^{85}$, $R^{86}$, $R^{87}$, $R^{88}$, $R^{89}$, $R^{90}$ groups are independently substituted or unsubstituted $C_{1-4}$ hydrocarbyl or nitrogen containing groups. In one preferred embodiment, the polysiloxane is a polyoxyethylene heptamethyl trisiloxane wherein $R^{81}$ is $-C_nH_{2n}O(CH_2CH_2O)_m$ $(CH_2CH(CH_3)O)_qX$, n is 3 or 4, a is 1, b is 0, m is 1 to about 30, q is 0, X is hydrogen or a methyl, ethyl or acetyl group, and the $R^{82}$, $R^{83}$, $R^{84}$, $R^{85}$, $R^{86}$, $R^{87}$, $R^{88}$, $R^{89}$ and $R^{90}$ groups are independently substituted or unsubstituted $C_{1-4}$ hydrocarbyl or nitrogen containing groups. In another preferred embodiment, a is 1 to 5, b is 0 to 10, n is 3 or 4, m is 1 to about 30, q is 0, X is hydrogen or a methyl, ethyl or acetyl group, and $R^{82}$, $R^{83}$, $R^{84}$, $R^{85}$, $R^{86}$, $R^{87}$, $R^{88}$, $R^{89}$ and $R^{90}$ are methyl groups. In another preferred embodiment, a is 1 to 5, b is 0 to 10, n is 3 or 4, m is 4 to 12, q is 0, X is hydrogen or a methyl or acetyl group, $R^{82}$, $R^{83}$, $R^{84}$, $R^{85}$, $R^{86}$, $R^{87}$, $R^{88}$, $R^{89}$ and $R^{90}$ are methyl groups. In a more preferred embodiment, a is 1, b is 0, n is 3 or 4, m is 1 to about 30, b is 0, X is hydrogen or a methyl, ethyl or acetyl group, and $R^{82}$, $R^{83}$, $R^{84}$, $R^{85}$, $R^{86}$, $R^{87}$, $R^{88}$, $R^{89}$ and $R^{90}$ are methyl groups. In a further preferred embodiment, a is 1, b is 0, n is 3, m is 8, b is 0, X is methyl and $R^{82}$, $R^{83}$, $R^{84}$, $R^{85}$, $R^{86}$, $R^{87}$, $R^{88}$, $R^{89}$ and $R^{90}$ are methyl groups. Trisiloxanes of the above formula are generally described in product literature of Crompton Corporation and in U.S. Pat. No. 3,505,377. Several of such trisiloxanes are ethoxylated organosilicone wetting agents available from Crompton Corporation as Silwet® silicone glycol copolymers. Both liquid organosilicones and dry organosilicones can be used in the surfactant composition; both are included within the scope of the invention. Examples of trisiloxanes are those sold commercially in the United States or elsewhere by Crompton Corporation as Silwet® L-77, Silwet® 408 and Silwet® 800, by Dow-Corning as Sylgard® 309, by Exacto, Inc., as Qwikwet® 100, and by Goldschmidt as Breakthru S-240. In the most preferred polyoxyethylene heptamethyl trisiloxanes, $R^2$ is hydrogen.

Polyoxyalkylene alcohols have the formula:

(13)

wherein $R^{91}$ is hydrocarbyl or substituted hydrocarbyl having from 1 to about 30 carbon atoms, $R^{92}$ in each of the $(R^{92}O)_x$ groups is independently $C_2$-$C_4$ alkylene, $R^{93}$ is hydrogen, or a linear or branched alkyl group having from 1 to about 4 carbon atoms, and x is an average number from 1 to about 60.

Alkoxylated dialkylphenols have the formula:

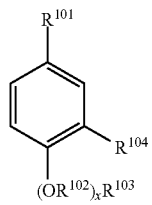

(14)

wherein $R^{101}$ and $R^{104}$ are independently hydrogen, or a linear or branched alkyl group having from 1 to about 30 carbon atoms and at least one of $R^{101}$ and $R^{104}$ is an alkyl group, $R^{102}$ in each of the $(R^{102}O)_x$ groups is independently $C_2$-$C_4$ alkylene, $R^{103}$ is hydrogen, or a linear or branched alkyl group having from 1 to about 4 carbon atoms, and x is an average number from 1 to about 60.

Other additives, adjuvants, or ingredients may be introduced into the formulations of the present invention to improve certain properties of the resulting formulations. For example, safeners, such as ferric sulfate, citric acid or furilazole, can be included in the compositions of the present invention. Further, although the formulations of the present invention generally show good overall stability and compatibility without the addition of any further additives, the presence of an additional compatibilizer (also commonly referred to as a cloud point enhancer or stabilizer) can improve the properties of the formulations of the present invention. It has been found that a subset of the above described cationic surfactants, including a $C_4$ to $C_{16}$ alkyl or aryl amine compound, or the corresponding quaternary ammonium compound, can enhance the compatibility of certain glyphosate salts (e.g., potassium or isopropylamine) with surfactants that otherwise exhibit low or marginal compatibility at a given glyphosate loading. Examples of some suitable such compatibilizers include primary, secondary or tertiary $C_4$ to $C_{16}$ alkyl or aryl amine compounds, or the corresponding quaternary ammonium compounds. For example, in some embodiments, the cationic compatibilizer compounds have the formula:

$$R^{111}-N\begin{matrix}R^{112}\\ \\R^{113}\end{matrix} \quad \text{or} \tag{15}$$

$$R^{111}-\underset{\underset{R^{114}}{|}}{\overset{\overset{R^{112}}{|}}{N^+}}-R^{113} \quad A^- \tag{16}$$

wherein $R^{111}$ is linear or branched alkyl or aryl having from about 4 to about 16 carbon atoms; $R^{112}$ and $R^{113}$ are hydrogen, methyl or ethyl; $R^{114}$ is hydrogen or methyl; and $A^-$ is an agriculturally acceptable anion. Examples of suitable additional compatibilizers for use with the formulations of the present invention include, for example, cocoamine (Armeen C), dimethylcocoamine (Arquad DMCD) and cocoammonium chloride (Arquad C) all of which are available from Akzo Nobel (California).

The present invention also includes a method for killing or controlling weeds or unwanted vegetation comprising the steps of forming an application mixture of a composition of the present invention and applying a herbicidally effective amount of the application mixture to the foliage of the weeds or unwanted vegetation. The present invention also includes a method for killing or controlling weeds or unwanted vegetation comprising the steps of diluting a liquid concentrate of the present invention in a convenient amount of water to form an application mixture (also known as a tank mix) and applying a herbicidally effective amount of the application mixture to the foliage of the weeds or unwanted vegetation. Similarly included in the invention is the method of killing or controlling weeds or unwanted vegetation comprising the steps of dissolving and diluting a solid particulate concentrate of the present invention in a convenient amount of water to form an application mixture and applying a herbicidally effective amount of the application mixture to the foliage of the weeds or unwanted vegetation.

In herbicidal methods of the present invention of using a composition of the invention, the application mixture is applied to the foliage of a plant or plants at an application rate sufficient to give a desired herbicidal effect. This application rate is usually expressed as amount of glyphosate per unit area treated, e.g., grams acid equivalent per hectare ("g a.e./ha"). What constitutes a "desired herbicidal effect" is, typically and illustratively, at least 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

In the context of surfactant content or glyphosate salt content, the expression "predominantly comprises" means that at least about 50%, preferably at least about 75% and more preferably at least about 90%, by weight of the surfactant component is made up of surfactants having the specified features of molecular structure or of glyphosate salt.

When a maximum or minimum "average number" is recited herein with reference to a structural feature such as oxyethylene units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Having described the invention in detail, it will be apparent that modifications and variations are possible without departing from the scope of the invention defined in the appended claims.

EXAMPLES

The following non-limiting examples are provided to further illustrate the present invention.

The components in the Table below are used in the Examples:

| Component | Description |
|---|---|
| AGM550 | Huntsman Surfonic AGM-550 surfactant |
| T105 | Ethomeen T105 tallowamine ethoxylate 10.5 EO surfactant (available from Akzo Nobel) |
| T20 | Ethomeen T20 tallowamine ethoxylate 10 EO surfactant (available from Akzo Nobel) |
| T80 | Ethomeen T80 tallowamine ethoxylate 8 EO surfactant (available from Akzo Nobel) |
| C12 | Ethomeen C12 cocoamine ethoxylate 2 EO surfactant (available from Akzo Nobel) |
| C15 | Ethomeen C15 cocoamine ethoxylate 5 EO surfactant (available from Akzo Nobel) |
| T20/C12 | 55:45 blend of Ethomeen T20 tallowamine ethoxylate 10 EO surfactant and Ethomeen C12 cocoamine ethoxylate 2 EO surfactant |
| $Fe_2(SO_4)_3$ | Ferric sulfate |
| Citric | Citric Acid |
| DF6889 | Agnique DF6889 20% solution of silicone antifoam (available from Cognis) |
| Dopant | $Fe_2(SO_4)_3$ and Citric Acid blend |

Example 1

An experiment was performed to determine the efficacy of experimental application mixtures prepared by dilution of experimental glyphosate concentrate formulations containing a blend of etheramine, tallowamine and cocoamine surfactants relative to comparative application mixtures prepared by dilution of comparative glyphosate concentrate formulations containing (i) a blend of tallowamine and cocoamine surfactants (comparative formulation A—"Comp A") or (ii) an etheramine surfactant (comparative formulation B—"Comp B"). Experimental and comparative formulations containing 540 grams a.e. per liter (39.7 weight percent a.e.) of potassium glyphosate, the surfactant blend and other components were prepared with the components as indicated in Table 1a wherein the percentage by weight of each surfactant of the total surfactant loading is indicated in parentheses. All values are in weight percent unless indicated otherwise.

The efficacy of application mixtures prepared from the Table 1a formulations was evaluated on velvetleaf (ABUTH) and prickly sida (SIDSP). The efficacy trials were conducted under hot greenhouse conditions (29.4° C. days and 21.1° C. nights). For each trial, glyphosate was applied at four rates; 213, 320, 561, and 841 grams a.e./ha in the equivalent of 93 liters per hectare of water. Ratings were taken at 20 days after treatment ("DAT"). The results at the four rates were combined for the overall ratings.

The result of the efficacy trials is reported in Table 1b as t-test pairwise mean difference comparisons of the comparative formulations versus the experimental formulations wherein the percentage of AGM550 surfactant of the total surfactant loading is indicated in parentheses. A negative difference value indicates that the experimental formulation provided increased efficacy relative to the comparative formulations. For instance, in Table 1b, Comp A, containing only the mixed alkylamine surfactants gave weed control equal to or less than that of the experimental formulations containing the blended surfactants in all cases for the formulations containing 135 grams/liter of surfactant (Series A experimental formulations). Two of the formulations were superior to Comp A on both weeds and formulation A59 was superior on ABUTH. Even for the formulations of series B experimental formulations which contained less total surfactant, the formulations containing blended surfactants were superior for both weeds for two formulations and ABUTH for the other. In comparison with the comparative formulation containing only the etheramine surfactant (Comp B), all of the experimental formulations containing the blended surfactants were superior on ABUTH and three of them were essentially equal on SIDSP.

TABLE 1a

| | Series A | | | |
|---|---|---|---|---|
| Formulation | A74 | A59 | A44 | Comp. A |
| AGM550 | 7.35% (74) | 5.88% (59) | 4.41% (44) | 0.00% (0) |
| T105 | 1.32% (13) | 2.21% (22) | 3.09% (31) | 5.50% (55) |
| C12 | 1.25% (13) | 1.84% (19) | 2.43% (25) | 4.50% (45) |
| $Fe_2(SO_4)_3$ | 346 ppm | 346 ppm | 346 ppm | 346 ppm |
| Citric | 0.24% | 0.24% | 0.24% | 0.24% |
| DF6889 | 0.01% | 0.01% | 0.01% | 0.01% |
| Density | 1.36 g/mL | 1.36 g/mL | 1.36 g/mL | 1.36 g/mL |
| Total Surfactant | 135 g/L | 135 g/L | 135 g/L | 135 g/L |
| Cloud Point | 58° C. | 66° C. | 61° C. | 65° C. |

| | Series B | | | |
|---|---|---|---|---|
| Formulation | B74 | B59 | B4 | Comp. B |
| AGM550 | 6.54% (74) | 5.22% (59) | 3.9% (44) | 7.48% (100) |
| T105 | 1.25% (14) | 1.99% (23) | 2.72% (31) | 0.00% (0) |
| C12 | 1.03% (12) | 1.62% (18) | 2.21% (25) | 0.00% (0) |
| $Fe_2(SO_4)_3$ | 346 ppm | 346 ppm | 346 ppm | 346 ppm |
| Citric | 0.24% | 0.24% | 0.24% | 0.24% |
| DF6889 | 0.01% | 0.01% | 0.01% | 0.01% |
| Density | 1.36 g/mL | 1.36 g/mL | 1.36 g/mL | 1.36 g/mL |
| Total Surfactant | 120 g/L | 120 g/L | 120 g/L | 120 g/L |
| Cloud Point | 68° C. | 71° C. | 66° C. | 70° C. |

TABLE 1b

| Comp. B | Weeds Combined All Data | n | Individual Weed Species ABUTH | n | SIDSP | n |
|---|---|---|---|---|---|---|
| Total surfactant loading of 120 g/L ||||||||
| B74 (74) | −2.4 | 48 | −4.6 | 24 | −0.1 | 24 |
| B44 (44) | 0.0 | 48 | −3.8 | 24 | 3.8 | 24 |
| B59 (59) | 1.1 | 48 | −3.0 | 24 | 5.1 | 24 |
| Total surfactant loading of 135 g/L ||||||||
| A44 (44) | −2.8 | 48 | −5.7 | 24 | 0.1 | 24 |
| A74 (74) | −1.5 | 48 | −2.0 | 24 | −1.1 | 24 |
| A59 (59) | 0.7 | 48 | −3.2 | 24 | 4.6 | 24 |

| Comp. A | Weeds Combined All Data | n | Individual Weed Species ABUTH | n | SIDSP | n |
|---|---|---|---|---|---|---|
| Total surfactant loading of 120 g/L ||||||||
| B74 (74) | −4.8 | 48 | −4.9 | 24 | −4.7 | 24 |
| B44 (44) | −2.5 | 48 | −4.2 | 24 | −0.8 | 24 |
| B59 (59) | −1.4 | 48 | −3.3 | 24 | 0.6 | 24 |
| Total surfactant loading of 135 g/L ||||||||
| A44 (44) | −5.2 | 48 | −6.0 | 24 | −4.4 | 24 |
| A74 (74) | −4.0 | 48 | −2.3 | 24 | −5.6 | 24 |
| A59 (59) | −1.7 | 48 | −3.5 | 24 | 0.0 | 24 |

The Table 1a formulations were diluted to form application mixtures that were then applied to velvetleaf (ABUTH), sicklepod (CASOB), morningglory (IPOHE), hemp sesbania (SEBEX), barnyardgrass (ECHCG), smooth pigweed (AMACH), brackenfern (POLPY) and giant foxtail (SETFA) plants in field efficacy trials. The efficacy trials were conducted under hot greenhouse conditions (29.4° C. days and 21.1° C. nights). For each trial, glyphosate was applied at four rates; 213, 320, 561, and 841 grams a.e./ha in the equivalent of 93 liters per hectare of water. Ratings were taken at 20 days after treatment ("DAT"). The results at the four rates were combined for the overall ratings. The efficacy of the experimental formulations was evaluated against application mixtures prepared from Comp. A and Comp. B. The result of the efficacy field trials is reported in Table 1c as t-test pairwise mean comparisons of the standards versus the experimental formulations wherein the weight percentage of AGM550 surfactant of the total surfactant loading is indicated in parentheses.

TABLE 1c

| Comp. B versus | Combined species All Data | n |
|---|---|---|
| Total surfactant loading of 120 g/L |||
| B74 (74) | −2.3 | 336 |
| B59 (59 | −1.8 | 336 |
| B44 (44) | −0.3 | 336 |
| Total surfactant loading of 135 g/L |||
| A74 (74) | −2.0 | 336 |
| A59 (59) | −2.0 | 336 |
| A44 (44) | −1.2 | 336 |

TABLE 1c-continued

| Comp. B versus | Individual Weed Species ABUTH | n | CASOB | n |
|---|---|---|---|---|
| Total surfactant loading of 120 g/L |||||
| B74 (74) | −0.5 | 80 | −6.7 | 32 |
| B59 (59 | −0.9 | 80 | −3.9 | 32 |
| B44 (44) | −0.7 | 80 | 0.3 | 32 |
| Total surfactant loading of 135 g/L |||||
| A74 (74) | 0.1 | 80 | −5.9 | 32 |
| A59 (59) | −0.6 | 80 | −.28 | 32 |
| A44 (44) | −0.3 | 80 | −4.4 | 32 |

| Comp. B versus | Individual Weed Species IPOHE | n | SEBEX | n | ECHCG | n |
|---|---|---|---|---|---|---|
| Total surfactant loading of 120 g/L |||||||
| B74 (74) | −1.0 | 64 | −4.7 | 80 | −2.2 | 32 |
| B59 (59) | −2.4 | 64 | −2.4 | 80 | −0.8 | 32 |
| A44 (44) | −2.3 | 64 | −2.0 | 80 | 1.7 | 32 |
| Total surfactant loading of 135 g/L |||||||
| A74 (74) | −2.3 | 64 | −3.8 | 80 | −1.3 | 32 |
| A59 (59) | −4.7 | 64 | −2.3 | 80 | −1.7 | 32 |
| A44 (44) | −0.9 | 64 | 0.6 | 80 | −1.1 | 32 |

| Comp. B versus | Individual Weed Species AMACH | n | POLYP | n | SETFA | n |
|---|---|---|---|---|---|---|
| Total surfactant loading of 120 g/L |||||||
| B74 (74) | 0.3 | 16 | 0.3 | 16 | No Sig. Diff. | 16 |
| B59 (59) | −0.6 | 16 | −1.3 | 16 | No Sig. Diff | 16 |
| B44 (44) | −0.6 | 16 | 0.8 | 16 | No Sig. Diff | 16 |
| Total surfactant loading of 135 g/L |||||||
| A74 (74) | 0.3 | 16 | −0.7 | 16 | No Sig. Diff | 16 |
| A59 (59) | 1.9 | 16 | −1.5 | 16 | No Sig. Diff | 16 |
| A44 (44) | −0.4 | 16 | −0.9 | 16 | No Sig. Diff | 16 |

| Comp. A versus | Weeds Combined All Data | n | Individual Weed Species ABUTH | n | CASOB | n |
|---|---|---|---|---|---|---|
| Total surfactant loading of 120 g/L |||||||
| B74 (74) | −0.6 | 336 | 0.6 | 80 | −3.8 | 32 |
| B59 (59) | −0.2 | 336 | 0.2 | 80 | −0.9 | 32 |
| B44 (44) | 1.3 | 336 | 0.4 | 80 | 3.3 | 32 |
| Total surfactant loading of 135 g/L |||||||
| A74 (74) | −0.4 | 336 | 1.2 | 80 | −1.0 | 32 |
| A59 (59) | −0.4 | 336 | 0.5 | 80 | 0.2 | 32 |
| A44 (44) | 0.4 | 336 | 0.8 | 80 | −1.4 | 32 |

| Comp. A versus | Individual Weed Species IPOHE | n | SEBEX | n | ECHCG | n |
|---|---|---|---|---|---|---|
| Total surfactant loading of 120 g/L |||||||
| B74 (74) | 0.8 | 64 | −2.1 | 80 | −1.0 | 32 |
| B59 (59) | −0.6 | 64 | 0.3 | 80 | 0.4 | 32 |
| B44 (44) | 0.9 | 64 | 3.3 | 80 | 0.1 | 32 |

TABLE 1c-continued

| Total surfactant loading of 135 g/L | | | | | | |
|---|---|---|---|---|---|---|
| A74 (74) | −0.5 | 64 | −1.2 | 80 | −0.1 | 32 |
| A59 (59) | −2.9 | 64 | 0.4 | 80 | −0.5 | 32 |
| A44 (44) | −0.5 | 64 | 0.7 | 80 | 2.8 | 32 |

| | Individual Weed Species | | | | | |
|---|---|---|---|---|---|---|
| Comp. A versus | AMACH | n | POLYP | n | SETFA | n |
| Total surfactant loading of 120 g/L | | | | | | |
| B74 (74) | 0.1 | 16 | 0.0 | 16 | No Sig. Diff. | 16 |
| B59 (59) | −0.8 | 16 | −1.6 | 16 | No Sig. Diff. | 16 |
| B44 (44) | −0.6 | 16 | −1.3 | 16 | No Sig. Diff. | 16 |
| Total surfactant loading of 135 g/L | | | | | | |
| A74 (74) | 0.1 | 16 | −1.0 | 16 | No Sig. Diff. | 16 |
| A59 (59) | 1.7 | 16 | −1.8 | 16 | No Sig. Diff. | 16 |
| A44 (44) | −0.8 | 16 | 0.5 | 16 | No Sig. Diff. | 16 |

With the exception of formulation B44 (which contains a lower concentration of surfactant), the experimental formulations appear to be equally efficacious across a wide variety of narrowleaf and broadleaf weeds compared to Comp A. With the exception of formulation B44, which had efficacy similar to Comp B, the remaining formulations appear to be more efficacious across a wide variety of narrowleaf and broadleaf weed compared to Comp. B. The overall trend appears to be that the blended surfactants contained in the experimental formulations are superior to the comparative formulations that contain only one of class of surfactant.

Example 2

An experiment was performed to determine the efficacy of experimental mixtures prepared by dilution of experimental concentrate formulations containing a blend of etheramine, tallowamine and cocoamine surfactants. Experimental formulations and comparative formulation Comp. C, each containing 540 grams a.e. per liter (39.7 weight percent a.e.) of potassium glyphosate, the surfactant blend and other components were prepared with the components and their concentration in weight percent as indicated in Table 2a wherein the percentage of each surfactant of the total surfactant loading is indicated in parentheses.

TABLE 2a

| Formulation | C8031 | C8011 | C8013 |
|---|---|---|---|
| AGM550 | 7.08 (80) | 7.08 (80) | 7.08 (80) |
| T20 | 0.01 | 0.01 | 0.01 |
| C15 | 1.357 | 1.357 | 1.357 |
| Dopant DF6889 | 0.77 | 0.77 | 0.77 |
| Density | | | |
| Total Surfactant | 8.85 | 8.85 | 8.85 |

| Formulation | C6511 | C6525 | C5014 | Comp. C |
|---|---|---|---|---|
| AGM550 | 5.75 (65) | 5.75 (65) | 4.43 (50) | 8.85 |
| T20 | 1.55 (17.5) | 0.89 (10) | 0.89 (10) | — |
| C15 | 1.55 (17.5) | 2.21 (25) | 3.54 (40) | — |
| Dopant | 0.77 | 0.77 | 0.77 | — |
| DF6889 | 0.01 | 0.01 | 0.01 | — |
| Density | 1.357 | 1.357 | 1.357 | 1.357 |
| Total Surfactant | 8.85 | 8.85 | 8.85 | 8.85 |

The Table 2a experimental and comparative formulations were diluted to form application mixtures and were applied postemergence to purselane (POROL) at rates of 320, 561 and 841 g a.e./ha in the equivalent of 93 liters per hectare of water under hot and dry green house conditions of 29.4° C. days and 21.1° C. nights. Herbicidal effectiveness was measured as percent plant control at 23 days after treatment ("DAT") by comparison with untreated plants, based on visual assessment by a technician trained in the art of making such assessments. Percent control results for the formulations and various commercial products are reported in Table 2b.

TABLE 2b

| POROL Control 23 DAT | | | |
|---|---|---|---|
| Formulation | 320 g a.e./ha | 561 g a.e./ha | 841 g a.e./ha |
| Comp. A | 50.8 | 90.8 | 94.5 |
| C8031 | 50.8 | 79.2 | 94.3 |
| C8011 | 40.8 | 84.7 | 91.8 |
| C8013 | 53.3 | 81.7 | 90.5 |
| C6511 | 43.3 | 76.7 | 92.2 |
| C6525 | 50 | 77.5 | 96.2 |
| C5014 | 50.8 | 79.2 | 95.5 |
| Comp. C | 51.7 | 78.3 | 90.8 |
| LSD | 7.3 | 7.9 | 4.4 |

The data from Table 2b were evaluated in a t-test analysis as compared to Comp. A (containing a mixed alkylamine surfactant system) and Comp. C (containing only etheramine surfactant). The data are presented in Table 2c wherein the percentage of AGM550 surfactant of the total surfactant loading is indicated in parentheses.

TABLE 2c

| Comp. C versus | POROL | n |
|---|---|---|
| Comp. A | −0.1 | 18 |
| C8013 (80) | −1.6 | 18 |
| C5014 (50) | −1.6 | 18 |
| C8031 (80) | −1.2 | 18 |
| C6525 (65) | −1.0 | 18 |
| C8011 (80) | 1.1 | 18 |
| C6511 (65) | 2.8 | 18 |

Experimental formulations C8013, C5014, C8031 and C6525 were equal or slightly superior to Comp C (containing only the etheramine surfactant). Experimental formulations C8011 and C6511 were equal or slightly inferior to Comp C. All experimental formulations were inferior to Comp A (containing the mixed alkylamine surfactant system). Note however that Comp A contained a higher total surfactant loading (10 wt %) than the experimental formulations (about 8.8 wt %) which may, as a result, skew the efficacy results.

Example 3

An experiment was performed to determine the efficacy of application mixtures prepared by dilution of experimental glyphosate concentrate formulations containing a blend of etheramine, tallowamine and cocoamine surfactants relative to comparative application mixtures prepared by dilution of comparative glyphosate concentrate formulations containing (i) an etheramine surfactant (comparative formulation D1—"Comp D1") or (ii) a blend of tallowamine and cocoamine surfactants (comparative formulation D2—"Comp D2"). Formulations containing 540 grams a.e. per liter (39.7 weight percent a.e.) of potassium glyphosate, the surfactant blend and other components were prepared with the components and their concentration in weight percent as indicated in Table 3a.

TABLE 3a

| Formulation | Comp. D1 | C75 | D50 | D25 | Comp. D2 |
|---|---|---|---|---|---|
| T20/C12 | — | 2.21 | 4.41 | 6.61 | 8.82 |
| AGM550 | 8.82 | 6.61 | 4.41 | 2.21 | — |
| DF6889 | 0.01 | 0.01 | 0.01 | 0.01 | 0.01 |
| Density | 1.357 | 1.357 | 1.357 | 1.357 | 1.357 |
| Total Surfactant | 8.82 | 8.82 | 8.82 | 8.82 | 8.82 |

The Table 3a experimental and comparative formulations were diluted to form application mixtures with the equivalent of 93 liters per hectare of water. The application mixtures were applied postemergence to velvetleaf (ABUTH) at rates of 280, 426, 561 and 841 g a.e./ha under hot and dry green house conditions of 29.4° C. days and 21.1° C. nights. Herbicidal effectiveness was measured as percent plant control at 20 DAT by comparison with untreated plants, based on visual assessment by a technician trained in the art of making such assessments. Percent control results for the formulations and various commercial products are reported in Table 3b wherein the percentage of AGM550 surfactant of the total surfactant loading is indicated in parentheses.

TABLE 3b

ABUTH Control 20 DAT

| Formulation | 280 g a.e./ha | 426 g a.e./ha | 561 g a.e./ha | 841 g a.e./ha |
|---|---|---|---|---|
| Comp. D1 | 25.8 | 63.3 | 85.8 | 90.8 |
| D75 (75) | 34.2 | 62.5 | 82.5 | 87.5 |
| D50 (50) | 43.3 | 59.2 | 77.5 | 90.8 |
| D25 (25) | 25.8 | 59.2 | 88.3 | 88.8 |
| Comp. D2 (0) | 28.3 | 59.2 | 76.7 | 88 |
| Comp. A | 25.8 | 52.7 | 82.7 | 90.5 |
| Comp. B | 25.8 | 62.5 | 84.2 | 92.2 |
| LSD | 9.4 | 5.9 | 5.1 | 5.3 |

All experimental formulations gave substantially equivalent efficacy for velvetleaf control as compared to Comp. D1 and Comp. D2. All experimental formulations gave substantially equivalent efficacy for velvetleaf control as compared to Comp. A (containing the mixed alkylamine surfactant system) and Comp. B (containing the etheramine surfactant). Note however that Comp. A contained a higher total surfactant loading (10 wt %) and Comp. B contained a lower total surfactant loading (about 7.5 wt %) than the experimental formulations (about 8.8 wt %) which may, as a result, skew the efficacy results.

Example 4

An experiment was performed to determine cloud points for experimental potassium glyphosate concentrate formulations containing a blend of etheramine, tallowamine and cocoamine surfactants versus comparative formulations containing (i) an etheramine surfactant or (ii) a blend of tallowamine and cocoamine surfactants as indicated in Tables 4a, 4b and 4c. The Table 4a formulations each contained about 540 g a.e./L potassium glyphosate, $Fe_2(SO_4)_3$ (about 346 ppm iron), Citric (about 0.24 wt. % citric acid) and DF111S (about 0.05 wt. % Agnique DFM 111S).

TABLE 4a

| C12 (wt. %) | T105 (wt. %) | AGM550 (wt. %) | Total Surfactant (g/L) | Cloud Point (° C.) |
|---|---|---|---|---|
| — | — | 10.0 | 135 | 52 |
| 4.5 | 5.5 | — | 135 | 64 |
| 1.1 | 1.4 | 7.5 | 135 | 58 |
| 1.5 | 1.8 | 6.7 | 135 | 55 |
| 2.2 | 2.8 | 5.0 | 135 | 58 |
| — | — | 9.2 | 125 | 59 |
| 4.1 | 5.1 | — | 125 | 69 |
| 1.0 | 1.3 | 6.9 | 125 | 59 |
| 1.4 | 1.7 | 6.1 | 125 | 62 |
| 2.1 | 2.5 | 4.6 | 125 | 65 |
| — | — | 8.5 | 115 | 64 |
| 3.8 | 4.7 | — | 115 | 71 |
| 1.0 | 1.2 | 6.3 | 115 | 66 |
| 1.3 | 1.5 | 5.7 | 115 | 65 |
| 1.9 | 2.3 | 4.3 | 115 | 68 |
| — | — | 7.7 | 105 | 67 |
| 3.5 | 4.2 | — | 105 | 81 |
| 0.9 | 1.1 | 5.8 | 105 | 66 |
| 1.1 | 1.4 | 5.2 | 105 | 69 |
| 1.7 | 2.1 | 3.9 | 105 | 72 |

TABLE 4b

| Glyphosate (g a.e./L) | C12 (wt. %) | T105 (wt. %) | AGM550 (wt. %) | Cloud Point (° C.) |
|---|---|---|---|---|
| 560 | 0.0 | 0.0 | 5.0 | 77 |
| 560 | 0.0 | 5.0 | 0.0 | not soluble |
| 560 | 0.0 | 2.5 | 2.5 | not soluble |
| 560 | 0.0 | 3.33 | 1.67 | not soluble |
| 560 | 0.5 | 2.0 | 2.5 | not soluble |
| 560 | 1.0 | 2.0 | 2.0 | 72 |
| 560 | 1.0 | 3.0 | 1.0 | not soluble |
| 560 | 1.5 | 1.0 | 2.5 | >90 |
| 560 | 1.5 | 1.5 | 2.0 | 88 |
| 560 | 1.67 | 1.67 | 1.67 | >90 |
| 560 | 2.0 | 1.0 | 2.0 | >90 |
| 560 | 2.0 | 2.0 | 1.0 | >90 |
| 560 | 2.5 | 2.5 | 0.0 | >90 |
| 560 | 2.5 | 0.0 | 2.5 | >90 |
| 560 | 3.33 | 0.0 | 1.67 | >90 |
| 560 | 3.33 | 1.67 | 0.0 | >90 |
| 560 | 5.0 | 0.0 | 0.0 | >90 |
| 580 | 0.5 | 2.0 | 2.5 | not soluble |
| 580 | 1.0 | 2.0 | 2.0 | 39 |
| 580 | 1.0 | 3.0 | 1.0 | not soluble |
| 580 | 1.5 | 1.0 | 2.5 | 84 |
| 580 | 1.5 | 1.5 | 2.0 | 79 |
| 580 | 1.67 | 1.67 | 1.67 | 86 |
| 580 | 2.0 | 1.0 | 2.0 | >90 |
| 580 | 2.0 | 2.0 | 1.0 | 87 |
| 600 | 0.0 | 0.0 | 5.0 | 57 |
| 600 | 0.0 | 5.0 | 0.0 | not soluble |
| 600 | 0.0 | 2.5 | 2.5 | not soluble |
| 600 | 0.0 | 3.33 | 1.67 | not soluble |
| 600 | 1.0 | 2.0 | 2.0 | 32 |
| 600 | 1.0 | 1.0 | 3.0 | 60 |
| 600 | 1.5 | 1.0 | 2.5 | 71 |
| 600 | 1.67 | 1.67 | 1.67 | 74 |
| 600 | 1.67 | 3.33 | 0.0 | not soluble |
| 600 | 1.67 | 0.0 | 3.33 | 87 |
| 600 | 2.0 | 1.0 | 2.0 | 88 |
| 600 | 2.0 | 2.0 | 1.0 | 77 |
| 600 | 2.0 | 3.0 | 0.0 | not soluble |

TABLE 4b-continued

| Glyphosate (g a.e./L) | C12 (wt. %) | T105 (wt. %) | AGM550 (wt. %) | Cloud Point (° C.) |
|---|---|---|---|---|
| 600 | 2.5 | 2.5 | 0.0 | 84 |
| 600 | 2.5 | 0.0 | 2.5 | >90 |
| 600 | 5.0 | 0.0 | 0.0 | >90 |

TABLE 4c

| Glyphosate (g a.e./L) | C12 (wt. %) | Tallowamine Type | Tallowamine wt. % | AGM550 (wt. %) | Cloud Point (° C.) |
|---|---|---|---|---|---|
| 540 | 1.2 | T105 | 1.4 | 7.4 | 51 |
| 540 | 1.0 | T105 | 1.2 | 6.6 | 68 |
| 540 | 1.9 | T105 | 2.3 | 6.0 | 62 |
| 540 | 1.6 | T105 | 2.0 | 5.3 | 68 |
| 540 | 2.5 | T105 | 3.1 | 4.4 | 64 |
| 540 | 2.2 | T105 | 2.7 | 4.0 | 70 |
| 540 | 0.7 | T80 | 1.9 | 7.4 | 57 |
| 540 | 1.0 | T80 | 1.3 | 6.6 | 71 |
| 540 | 1.4 | T80 | 4.1 | 4.4 | 51 |
| 540 | 1.3 | T80 | 3.7 | 4.0 | 62 |

The results show that by blending the two surfactants one can obtain improved physical properties, high cloud point, as compared to using the etheramine alone at the same surfactant concentration.

Example 5

An experiment was performed to determine the efficacy of application mixtures prepared by dilution of experimental glyphosate concentrate formulations containing a blend of etheramine, tallowamine and cocoamine surfactants relative to comparative application mixtures prepared by dilution of comparative glyphosate concentrate formulations containing (i) an etheramine surfactant (comparative formulation E1—"Comp. E1") or (ii) a blend of tallowamine and cocoamine surfactants (comparative formulation E2—"Comp. E2"). Formulations containing 540 grams a.e. per liter (39.7 weight percent a.e.) of potassium glyphosate, the surfactant blend and other components were prepared with the components and their concentration in weight percent as indicated in Table 5a.

TABLE 5a

| Formulation | Comp E1 | E80 | E50 | E20 | Comp E2 |
|---|---|---|---|---|---|
| T20/C12 | — | 1.17 | 4.43 | 7.08 | 8.85 |
| AGM550 | 8.85 | 7.08 | 4.43 | 1.17 | — |
| DF6889 | 0.01 | 0.01 | 0.01 | 0.01 | 0.01 |
| Density | 1.357 | 1.357 | 1.357 | 1.357 | 1.357 |
| Total Surfactant | 8.85 | 8.85 | 8.85 | 8.82 | 8.82 |

The Table 5a formulations were diluted to form application mixtures with the equivalent of 93 liters per hectare of water. The application mixtures were applied postemergence to velvetleaf (ABUTH) at rates of 280, 426, 561 and 841 g a.e./ha in the equivalent of 93 liters per hectare of water under normal green house conditions of 27° C. days and 21° C. nights. Herbicidal effectiveness was measured as percent plant control at 21 DAT by comparison with untreated plants, based on visual assessment by a technician trained in the art of making such assessments. The pairwise T-test comparisons of these formulations to the Comp E1 formulation are presented in Table 5b.

TABLE 5b

| Pairwise comparisons of control of ABUTH | | |
|---|---|---|
| Comp. E1 versus | Mean Diff | N |
| E80 | 1.0 | 24 |
| E50 | −0.4 | 24 |
| E20 | −0.2 | 24 |
| Comp. E2 | 0.0 | 24 |

All of the formulations gave statistically equivalent control of ABUTH. The experimental formulations gave slightly better results overall.

Example 6

The acute toxicity and irritation potential of several formulations of the present invention was evaluated. Formulations containing potassium glyphosate formulations containing various levels of potassium glyphosate and the surfactants AGM550 and T20/C15 were prepared as indicated in Table 6a where glyphosate concentration is reported in grams acid equivalent per liter and surfactant concentration is reported in grams per liter.

TABLE 6a

| Formulation | glyphosate | Total Surfactant | AGM550 | T20/C12 |
|---|---|---|---|---|
| 270P5P | 540 | 135 | 0 | 135 |
| 841R3Z | 480 | 90 | 90 | 0 |
| 105T8I | 540 | 115 | 92 | 23 |
| 252W1B | 480 | 140 | 112 | 28 |
| 790L0M | 540 | 120 | 120 | 0 |
| 460U7N | 540 | 135 | 135 | 0 |
| 106Y8D | 540 | 130 | 26 | 104 |
| 112O6H | 480 | 160 | 128 | 32 |

Eye and skin irritation for the formulations is reported in Table 6b as a numerical index along with the FIFRA (Federal Insecticide, Fungicide and Rodenticide Act) classification and FHSA (Federal Hazardous Substances Act) score associated with the findings. Eye and dermal irritation testing was done according to the methods provided in U.S. Environmental Protection Agency Office of Prevention, Pesticides and Toxic Substances, Health Effects Test Guidelines: OPPTS 870.2400 Acute Eye Irritation, August 1998; and OPPTS 870.2500 Acute Dermal Irritation, August 1998. In the eye irritation study, eyes of 6 rabbit animals were treated with the test article were scored for effects on the cornea, iris, and conjunctivae (redness, swelling and discharge). In the table the FHSA score represents the mean of these scores recorded 24, 48 and 72 hours following treatment versus a maximum score of 110. Similarly the Primary Irritation Index (PII) is the mean of the combined erythema and edema scores of the treated skin of 6 rabbit animals at 1, 24, 48 and 72 hours following removal of the test article versus a maximum score of 8. The FIFRA and FHSA results are presented in Table 6b.

TABLE 6b

| | Eye Irritation | | Skin Irritation | |
|---|---|---|---|---|
| Formulation | FIFRA category | FHSA score (max 110) | FIFRA category | PII (max 8) |
| 270P5P | 3 | 7.1 | 3 | 2.2 |
| 841R3Z | 3 | 7.8 | 3 | 2.2 |

TABLE 6b-continued

| | Eye Irritation | | Skin Irritation | |
|---|---|---|---|---|
| Formulation | FIFRA category | FHSA score (max 110) | FIFRA category | PII (max 8) |
| 105T8I | 3 | 8.2 | 4 | 1.5 |
| 252W1B | 3 | 17.7 | 3 | 2.2 |
| 790L0M | 3 | 19.4 | 4 | 1.9 |
| 460U7N | 3 | 29.7 | 2 | 4.9 |
| 106Y8D | 1 | 31.4 | 4 | 1.3 |
| 112O6H | 2 | 48 | 3 | 2.5 |

The data indicate that eye irritation generally increases as the load of AGM550 increases. The exception was formulation 106Y8D having a 1:4 ratio of AGM550 to T20/C12. Skin irritation, with the exception of 460U7N, was fairly constant across all formulations with Primary Irritation Indices in the range 1.5 to 2.5.

Additional acute toxicity studies were conducted on the formulations according to the methods provided in U.S. Environmental Protection Agency Office of Prevention, Pesticides and Toxic Substances, Health Effects Test Guidelines: OPPTS 870.1100 Acute Oral Toxicity, December 2002; OPPTS 870.1200 Acute Dermal Toxicity, August 1998; OPPTS 870.1300 Acute Inhalation Toxicity, August 1998; and OPPTS 870.2600 Skin Sensitization, March 2003. The results are reported in Table 6c where the limit for acute oral and dermal toxicity was conducted at 5000 milligrams per kilogram of body weight (mg/kg bw) and the limit test for acute inhalation toxicity was conducted at 2 milligrams per liter (mg/L) in air, and where "n.t." refers to not tested.

TABLE 6c

| Formulation | Rat Oral LD$_{50}$ mg/kg bw | Rat Dermal LD$_{50}$ mg/kg bw | Rat 4 hour inhalation LC$_{50}$ mg/L | Guinea Pig Dermal Sensitization Buehler test |
|---|---|---|---|---|
| 270P5P | >5000 | >5000 | >1.2 | negative |
| 841R3Z | n.t. | n.t. | n.t. | n.t. |
| 105T8I | n.t. | n.t. | >2.13 | n.t. |
| 252W1B | >5000 | >5000 | >2.03 | negative |
| 790L0M | n.t. | n.t. | n.t. | n.t. |
| 460U7N | >5000 | >5000 | >2.58 | negative |
| 106Y8D | n.t. | n.t. | n.t. | n.t. |
| 112O6H | n.t. | n.t. | n.t. | n.t. |

Example 7

An experiment was performed to determine the efficacy on velvetleaf (ABUTH) weeds and crop safety on Roundup Ready® corn for formulations containing a blend of etheramine, tallowamine and cocoamine surfactants. Formulations containing 540 grams a.e. per liter (39.7 weight percent a.e.; 1.36 g/L density) of potassium glyphosate, the surfactant blend and other components were prepared with the components and their concentration in weight percent as indicated in Table 7a wherein each formulation additional contained 0.01 weight percent DF6889 antifoam and formulations 301R5G, 937A3F and 937B8K each additionally contained 0.77 weight percent of a solution containing ferric sulfate and citric acid (4.5 percent iron).

TABLE 7a

| Formulation | glyphosate | AGM550 | T20/C12 |
|---|---|---|---|
| 790M9P | 39.7 | 8.85 | — |
| 301R5G | 39.7 | 7.08 | 1.77 |
| 937A3F | 39.7 | 4.43 | 4.43 |
| 937B8K | 39.7 | 1.77 | 7.08 |
| 937C2X | 39.7 | — | 8.85 |

The Table 7a formulations were diluted to form application mixtures and applied postemergence to velvetleaf (ABUTH) at rates of 280, 426, 561 and 841 g a.e./ha in the equivalent of 93 liters per hectare of water and to and Roundup Ready® corn at rates of 840, 1680 and 3360 g a.e./ha in the equivalent of 93 liters per hectare of water under hot and dry green house conditions of 29.4° C. days and 21.1° C. nights. Herbicidal effectiveness was measured as percent ABUTH control at 21 DAT and Roundup Ready® corn at 4 DAT by comparison with untreated plants, based on visual assessment by a technician trained in the art of making such assessments. Percent ABUTH control results are reported in Table 7b and percent Roundup Ready® corn control results are reported in Table 7c wherein the percentage of AGM550 surfactant of the total surfactant loading is indicated in parentheses. Roundup Ready® corn control is also referred to as crop injury.

TABLE 7b

| | ABUTH control 21 DAT | | | |
|---|---|---|---|---|
| Formulation | 280 g a.e./ha | 426 g a.e./ha | 561 g a.e./ha | 841 g a.e./ha |
| 790M9P (100) | 59.2 | 80.8 | 87.5 | 97.5 |
| 301R5G (80) | 60 | 79.2 | 87.5 | 94.2 |
| 937A3F (50) | 60.8 | 80 | 89.2 | 96.7 |
| 937B8K (20) | 57.5 | 80.8 | 89.2 | 97.5 |
| 937C2X (0) | 62.5 | 79.2 | 85 | 99.2 |
| Untreated ABUTH | 0 | 0 | 0 | 0 |

TABLE 7c

| | Roundup Ready ® corn control 4 DAT | | |
|---|---|---|---|
| Formulation | 840 g a.e./ha | 1680 g a.e./ha | 3360 g a.e./ha |
| 790M9P (100) | 2 | 7.5 | 13.8 |
| 301R5G (80) | 2 | 5 | 10 |
| 937A3F (50) | 0 | 4.3 | 6.3 |
| 937B8K (20) | 0 | 2 | 0 |
| 937C2X (0) | 0 | 0 | 0 |
| Untreated ABUTH | 0 | 0 | 0 |

The ABUTH and Roundup Ready® corn data was evaluated in a t-test analysis as compared to 301R5G having a surfactant component containing AGM550 and T20/C12 in a ratio of 4:1. The data are presented in Table 7d wherein the percentage of AGM550 surfactant of the total surfactant loading and the ratio of AGM550 surfactant to T20/C12 surfactant is indicated in parentheses.

TABLE 7d

| 301R5G versus | Mean Difference (ABUTH) | Mean Difference (Roundup Ready ® corn) |
|---|---|---|
| 790M9P (100) | −1.5 | −2.1 |
| 937A3F (50; 1:1) | −1.3 | 2.2 |
| 937B8K (20; 1:4) | −1 | 4.3 |
| 937C2X (0) | −1 | 5.7 |

The ABUTH data cannot be distinguished from formulation 301R5G. The Roundup Ready® corn data show that 937A3F, 937B8K and 937C2X formulations were significantly less efficacious than 301R5G (p<0.01) indicating that those formulations were less injurious to Roundup Ready® corn.

The ABUTH and Roundup Ready® corn data was evaluated in a t-test analysis as compared to 790M9P having a surfactant component containing only AGM550. The data are presented in Table 7e wherein the percentage of AGM550 surfactant of the total surfactant loading and the ratio of AGM550 surfactant to T20/C12 surfactant is indicated in parentheses.

TABLE 7E

| 790M9P versus | Mean Difference (ABUTH) | Mean Difference (Roundup Ready ® corn) |
|---|---|---|
| 937A3F (50; 1:1) | −0.4 | 4.3 |
| 937B8K (20; 1:4) | −0.2 | 6.4 |
| 937C2X (0) | 0 | 7.8 |
| 301R5G (80; 4:1) | 1.0 | 2.1 |

The ABUTH data cannot be distinguished from formulation 790M9P. The Roundup Ready® corn data show that 937A3F, 937B8K and 937C2X formulations were significantly less efficacious (p<0.01) than 301R5G indicating that those formulations were less injurious to Roundup Ready® corn.

The ABUTH and Roundup Ready® corn data was evaluated in a t-test analysis as compared to 937C2X having a surfactant component containing only T20/C12. The data are presented in Table 7f wherein the percentage of AGM550 surfactant of the total surfactant loading and the ratio of AGM550 surfactant to T20/C12 surfactant is indicated in parentheses.

TABLE 7f

| 937C2X versus | Mean Difference (ABUTH) | Mean Difference (Roundup Ready ® corn) |
|---|---|---|
| 937A3F (50; 1:1) | −0.2 | −3.5 |
| 790M9P (100) | 0.2 | −7.8 |
| 937B8K (20; 1:4) | 0.2 | −1.3 |
| 301R5G (80; 4:1) | 1.3 | −5.7 |

The ABUTH data cannot be distinguished from formulation 790M9P. The Roundup Ready® corn data show that 790M9P, 301R5G and 937A3F formulations were significantly more efficacious than 937C2X (p<0.01) indicating that those formulations were more injurious to Roundup Ready® corn.

The ABUTH efficacy data from Table 7b is presented in Table 7g in an ANOVA summary of formulations mean comparisons by rate. The percentage of AGM550 surfactant of the total surfactant loading is indicated in parentheses.

TABLE 7g

| Formulation | 280 g a.e./L | 426 g a.e./L | 561 g a.e./L | 841 g a.e./L |
|---|---|---|---|---|
| 790M9P (100) | 59.2 | 80.8 | 87.5 | 97.5 |
| 301R5G (80) | 60 | 79.2 | 87.5 | 94.2 |
| 937A3F (50) | 60.8 | 80 | 89.2 | 96.7 |
| 937B8K (20) | 57.5 | 80.8 | 89.2 | 97.5 |
| 937C2X (0) | 62.5 | 79.2 | 85 | 99.2 |
| LSD | 8 | 5.9 | 7.7 | 4.8 |

The Roundup Ready® corn efficacy (i.e., crop injury) data from Table 7c is presented in Table 7h in an ANOVA summary of formulations mean comparisons by rate. The percentage of AGM550 surfactant of the total surfactant loading is indicated in parentheses.

TABLE 7h

| Formulation | 840 g a.e./L | 1680 g a.e./L | 3360 g a.e./L |
|---|---|---|---|
| 790M9P (100) | 2 | 7.5 | 13.8 |
| 301R5G (80) | 2 | 5 | 10 |
| 937A3F (50) | 0 | 4.3 | 6.3 |
| 937B8K (20) | 0 | 2 | 2 |
| 937C2X (0) | 0 | 0 | 0 |
| LSD | 0 | 2.1 | 3.4 |

The overall Example 7 results show no significant differences between any of the formulations evaluated on ABUTH. All surfactant blend formulations (containing a AGM550-T20/C12 surfactant blend) were equivalent to 790M9P (containing only APG550 surfactant) and 937C2X (containing only T20/C12 surfactant).

The overall Example 7 results show that all three formulations containing the AGM550-T20/C12 surfactant blend were less injurious to Roundup Ready® corn than were formulation 790M9P (containing only AGM550 surfactant) and formulation 937C2X (containing only T20/C12 surfactant). The results show that the crop injury on Roundup Ready® corn decreases as the level of AGM550 surfactant in the formulation decreases.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. An herbicidal composition that is biologically effective to control growth of a susceptible plant, the composition comprising:
   a water-soluble herbicide comprising glyphosate or a derivative thereof;
   a surfactant component comprising an alkylamine alkoxylate surfactant and an etheramine alkoxylate surfactant wherein the alkylamine alkoxylate surfactant corresponds to the formula:

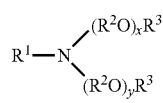

(1)

wherein
$R^1$ is $C_{12-18}$ straight or branched chain hydrocarbyl, each $R^2$ is independently $C_{1-4}$ alkylene, each $R^3$ is independently hydrogen or $C_{1-6}$ alkyl, and x+y is an average number of from about 5 to about 25 and the etheramine alkoxylate surfactant corresponds to the formula:

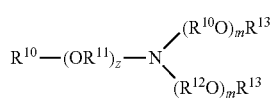

(2)

wherein $R^{10}$ is $C_{6-22}$ straight or branched chain hydrocarbyl, each $R^{11}$ is independently $C_{1-4}$ alkylene, each $R^{12}$ is independently $C_{1-4}$ alkylene, each $R^{13}$ is independently hydrogen or $C_{1-6}$ alkyl, z is an average number of from about 1 to about 10, m and n are average numbers such that m+n is in the range of from 2 to about 60, and
wherein the weight ratio of the etheramine alkoxylate surfactant to the alkylamine alkoxylate surfactant is from 70:30 to 50:50, and wherein:
the composition further comprises a compatibilizer surfactant of formula (4):

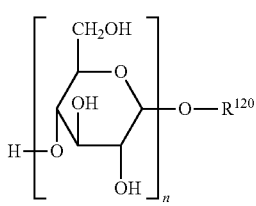

(4)

wherein $R^{120}$ is a branched or straight chain hydrocarbyl group having from about 4 to about 18 carbon atoms and n is an average number of from about 1 to about 5;
the weight ratio of the alkylamine alkoxylate surfactant of formula (1) to the compatibilizer is from about 80:20 to about 50:50; and
the composition is in the form of a single stable liquid phase.

2. The composition of claim 1 wherein $R^1$ is the $C_{12-18}$ alkyl, $R^2$ is $C_2$ alkylene, $R^3$ is hydrogen, and x+y is an average number of from about 8 to about 15.

3. The composition of claim 2 wherein $R^1$ is $C_{16-18}$ alkyl, $R^2$ is $C_2$ alkylene, $R^3$ is hydrogen, and x+y is an average number of from about 9 to about 10.

4. The composition of claim 1 wherein $R^{10}$ is $C_{12-18}$ alkyl, $R^{11}$ is isopropyl, $R^{12}$ is $C_2$ alkylene, $R^{13}$ is hydrogen, z is an average number of from about 1 to about 10 and m+n is an average number of from about 2 to about 20.

5. The composition of claim 4 wherein $R^{10}$ is $C_{12-14}$ alkyl, $R^{11}$ is isopropyl, $R^{12}$ is $C_2$ alkylene, $R^{13}$ is hydrogen, z is an average number of about 2 and m+n is an average number of about 5.

6. The composition of claim 1 wherein the weight ratio of glyphosate acid equivalent to the sum of the alkylamine alkoxylate surfactant of formula (2) and the etheramine alkoxylate surfactant of formula (1) or to the sum of the alkylamine alkoxylate surfactant of formula (2), the etheramine alkoxylate surfactant of formula (1) and the compatibilizer is from about 1:1 to about 6:1.

7. The composition of claim 1 wherein the glyphosate derivative is a glyphosate salt selected from the potassium salt, isopropylamine salt, di-ammonium salt, mono-ammonium salt, sodium salt, monoethanolamine salt, n-propylamine salt, methylamine salt, ethylamine salt, hexamethylenediamine salt, dimethylamine salt, trimethylsulfonium salt, triethanolamine salt, and mixtures thereof.

8. The composition of claim 1 wherein the composition is an aqueous herbicidal composition and the water soluble herbicide concentration is from about 0.01 to about 50 grams acid equivalent per liter.

9. The composition of claim 1 wherein the composition is an aqueous concentrate having a water soluble herbicide concentration of from about 300 grams acid equivalent per liter to a maximum concentration dictated by the solubility of the water-soluble herbicide.

10. The composition of claim 1 wherein the composition is an aqueous herbicidal composition having a pH of from about 4 to about 7.

11. The composition of claim 1 wherein the surfactant component further comprises at least one additional cationic surfactant, nonionic surfactant, or a combination thereof.

12. The composition of claim 1 wherein the composition is an aqueous composition and the composition further comprises a dicarboxylic acid compound selected from the group consisting of a dicarboxylic acid or a salt or ester thereof and wherein the weight ratio of total surfactant to the dicarboxylic acid compound is from 1:1 to about 50:1.

13. The composition of claim 1 wherein n is an average number between about 1 and about 3.

14. The composition of claim 1 wherein the weight ratio range of the alkylamine alkoxylate surfactant to the compatibilizer surfactant is from about 65:35 to about 50:50.

15. The composition of claim 1 wherein the water soluble herbicide comprises potassium glyphosate.

16. The composition of claim 1 wherein the weight ratio range of the etheramine alkoxylate surfactant to the sum of the alkylamine alkoxylate surfactant and compatibilizer surfactant is from about 80:20 to about 40:60.

* * * * *